US008308644B2

(12) United States Patent
McMorrow et al.

(10) Patent No.: US 8,308,644 B2
(45) Date of Patent: Nov. 13, 2012

(54) INSTANTANEOUS ULTRASONIC MEASUREMENT OF BLADDER VOLUME

(75) Inventors: Gerald McMorrow, Kirkland, WA (US); Henri Baartmans, HT IJsselstein (NL); Nicolaas Bom, NA Berkenwoude (NL); Charles Theodoor Lancee, PH Hoogersmilde (NL)

(73) Assignee: Verathon Inc., Bothell, WA (US)

( * ) Notice: Subject to any disclaimer, the term of this patent is extended or adjusted under 35 U.S.C. 154(b) by 334 days.

(21) Appl. No.: 10/523,681

(22) PCT Filed: Jul. 1, 2003

(86) PCT No.: PCT/EP03/07807
§ 371 (c)(1),
(2), (4) Date: Sep. 23, 2005

(87) PCT Pub. No.: WO2004/017834
PCT Pub. Date: Mar. 4, 2004

(65) Prior Publication Data
US 2006/0111633 A1    May 25, 2006

(30) Foreign Application Priority Data
Aug. 9, 2002 (GB) .................................. 0218547.8

(51) Int. Cl.
*A61B 8/00* (2006.01)

(52) U.S. Cl. ........ 600/443; 600/439; 600/449; 600/456; 600/437; 600/587

(58) Field of Classification Search .................. 600/407, 600/427, 437, 410, 443, 587, 456, 449
See application file for complete search history.

(56) References Cited

U.S. PATENT DOCUMENTS
3,613,069 A    10/1971    Cary, Jr.
(Continued)

FOREIGN PATENT DOCUMENTS
EP    0 271 214    6/1988
(Continued)

OTHER PUBLICATIONS

Hamilton; Nonlinear Acoustics; 1998; pp. 65-150. Please see pp. 132-133 regarding the use of Goldberg numbers; Academic Press; San Diego, CA USA.

(Continued)

*Primary Examiner* — Brian Casler
*Assistant Examiner* — Joel Lamprecht
(74) *Attorney, Agent, or Firm* — Scott Born; Foster Pepper PLLC

(57) ABSTRACT

An apparatus and methods to quantify the volume of urine in a human bladder with a limited number of acoustic beams is disclosed. In a first version the apparatus is composed of a transducers assembly that transmits a plurality of narrow ultrasound beams in different directions towards the bladder and receives the returning ultrasound signals; a receiver detector for processing the returned signals; an analog-to-digital converter; a memory to store the digitized data and a volume display allowing to define the optimal position of the transducer assembly. The apparatus also includes a signal processing software that automatically determines the bladder Depth D and Height H and computes the volume of urine using an empirical formula corrected by specific, empirically measured, filling dependant correction factors. In a second version a single wide angle ultrasound beam transducer transmitting ultrasound signals at fundamental frequency is used to quantify the urine volume. Return signals originating from a depth beyond the usual position of the posterior wall depth of a filled bladder are analyzed for presence of higher harmonic signals which in turn are related to presence or absence of urine. Both methods or a combination thereof can be used us a simple warning device for presence of residual urine after voiding or indicate the presence of a critical bladder urine filling level.

39 Claims, 11 Drawing Sheets

U.S. PATENT DOCUMENTS

| | | | | |
|---|---|---|---|---|
| 4,431,007 A | 2/1984 | Amazeen et al. | | 128/660 |
| 4,556,066 A | 12/1985 | Semrow | | 128/660 |
| 4,757,821 A | 7/1988 | Snyder | | 128/660 |
| 4,771,205 A | 9/1988 | Mequio | | 310/334 |
| 4,821,210 A | 4/1989 | Rumbaugh | | 364/518 |
| 4,844,080 A | 7/1989 | Frass et al. | | 128/660.01 |
| 4,926,871 A | 5/1990 | Ganguly et al. | | 128/660.07 |
| 5,058,591 A | 10/1991 | Companion et al. | | 128/661.03 |
| 5,060,515 A | 10/1991 | Kanda et al. | | 73/602 |
| 5,078,149 A | 1/1992 | Katsumata et al. | | 128/662.03 |
| 5,125,410 A | 6/1992 | Misono et al. | | 128/662.06 |
| 5,148,809 A | 9/1992 | Biegeleisen-Knight et al. | | 128/660.07 |
| 5,151,856 A | 9/1992 | Halmann et al. | | 364/413.03 |
| 5,159,931 A | 11/1992 | Pini | | 128/660.07 |
| 5,197,019 A | 3/1993 | Delon-Martin et al. | | 364/563 |
| 5,235,985 A | 8/1993 | McMorrow et al. | | 128/660.07 |
| 5,265,614 A | 11/1993 | Hayakawa et al. | | 128/602.03 |
| 5,299,577 A | 4/1994 | Brown et al. | | 128/660.07 |
| 5,381,794 A | 1/1995 | Tei et al. | | 128/662.03 |
| 5,432,310 A | 7/1995 | Stoeger | | 200/82 R |
| 5,435,310 A | 7/1995 | Sheehan et al. | | 128/653.1 |
| 5,465,721 A | 11/1995 | Kishimoto et al. | | 128/660.07 |
| 5,473,555 A | 12/1995 | Potter | | 364/724.1 |
| 5,487,388 A | 1/1996 | Rello et al. | | 128/660.09 |
| 5,503,152 A | 4/1996 | Oakley et al. | | 128/661.01 |
| 5,503,153 A | 4/1996 | Liu et al. | | 128/661.08 |
| 5,526,816 A | 6/1996 | Arditi | | 128/662.02 |
| 5,553,618 A | 9/1996 | Suzuki et al. | | 128/653.1 |
| 5,575,286 A | 11/1996 | Weng et al. | | 128/653.1 |
| 5,575,291 A | 11/1996 | Hayakawa et al. | | 128/662.03 |
| 5,577,506 A | 11/1996 | Dias | | 128/662.03 |
| 5,588,435 A | 12/1996 | Weng et al. | | 128/660.07 |
| 5,601,084 A | 2/1997 | Sheehan et al. | | 128/661.04 |
| 5,605,155 A | 2/1997 | Chalana et al. | | 128/660.07 |
| 5,615,680 A | 4/1997 | Sano | | 128/661.09 |
| 5,644,513 A | 7/1997 | Rudin et al. | | 364/572 |
| 5,645,077 A | 7/1997 | Foxlin | | 128/774 |
| 5,697,525 A | 12/1997 | O'Reilly et al. | | 222/105 |
| 5,698,549 A | 12/1997 | Steers et al. | | 514/211 |
| 5,724,101 A | 3/1998 | Haskin | | 348/441 |
| 5,735,282 A | 4/1998 | Hossack | | 128/662.03 |
| 5,738,097 A | 4/1998 | Beach et al. | | 128/661.09 |
| 5,776,063 A | 7/1998 | Dittrich et al. | | |
| 5,782,767 A | 7/1998 | Pretlow, III | | 600/443 |
| 5,806,521 A | 9/1998 | Morimoto et al. | | 128/661.01 |
| 5,841,889 A | 11/1998 | Seyed-Bolorforosh | | 382/128 |
| 5,846,202 A | 12/1998 | Ramamurthy et al. | | 600/450 |
| 5,851,186 A | 12/1998 | Wood et al. | | 600/437 |
| 5,873,829 A | 2/1999 | Kamiyama et al. | | 600/443 |
| 5,892,843 A | 4/1999 | Zhou et al. | | 382/176 |
| 5,898,793 A | 4/1999 | Karron et al. | | 382/131 |
| 5,903,664 A | 5/1999 | Hartley et al. | | 382/154 |
| 5,908,390 A | 6/1999 | Matsushima | | 600/447 |
| 5,913,823 A | 6/1999 | Hedberg et al. | | 600/443 |
| 5,928,151 A | 7/1999 | Hossack et al. | | 600/443 |
| 5,945,770 A | 8/1999 | Hanafy | | 310/322 |
| 5,964,710 A | 10/1999 | Ganguly et al. | | 600/449 |
| 5,971,923 A | 10/1999 | Finger | | 600/437 |
| 5,972,023 A | 10/1999 | Tanner et al. | | 606/219 |
| 5,980,459 A | 11/1999 | Chiao et al. | | 600/447 |
| 5,993,390 A | 11/1999 | Savord et al. | | 600/437 |
| 6,008,813 A | 12/1999 | Lauer et al. | | 345/424 |
| 6,030,344 A | 2/2000 | Guracar et al. | | 600/437 |
| 6,042,545 A | 3/2000 | Hossack et al. | | 600/443 |
| 6,048,312 A | 4/2000 | Ishrak et al. | | 600/443 |
| 6,063,033 A | 5/2000 | Haider et al. | | 600/447 |
| 6,064,906 A | 5/2000 | Langberg et al. | | 600/518 |
| 6,071,242 A * | 6/2000 | Lin | | 600/456 |
| 6,102,858 A * | 8/2000 | Hatfield et al. | | 600/443 |
| 6,106,465 A | 8/2000 | Napolitano et al. | | 600/443 |
| 6,110,111 A | 8/2000 | Barnard | | 600/438 |
| 6,117,080 A | 9/2000 | Schwartz | | 600/443 |
| 6,122,538 A | 9/2000 | Sliwa, Jr. et al. | | 600/407 |
| 6,123,669 A | 9/2000 | Kanda | | 600/443 |
| 6,126,598 A | 10/2000 | Entrekin et al. | | 600/437 |
| 6,142,942 A | 11/2000 | Clark | | 600/443 |
| 6,146,330 A | 11/2000 | Tsujino et al. | | |
| 6,148,095 A | 11/2000 | Prause et al. | | 382/131 |
| 6,151,404 A | 11/2000 | Pieper | | 382/128 |
| 6,159,150 A | 12/2000 | Yale et al. | | 600/437 |
| 6,171,248 B1 | 1/2001 | Hossack et al. | | 600/459 |
| 6,193,657 B1 | 2/2001 | Drapkin | | 600/437 |
| 6,200,266 B1 | 3/2001 | Shokrollahi et al. | | 600/438 |
| 6,210,327 B1 | 4/2001 | Brackett et al. | | 600/437 |
| 6,213,949 B1 * | 4/2001 | Ganguly et al. | | 600/449 |
| 6,213,951 B1 | 4/2001 | Krishnan et al. | | 600/458 |
| 6,222,948 B1 | 4/2001 | Hossack et al. | | 382/294 |
| 6,233,480 B1 | 5/2001 | Hochman et al. | | 600/476 |
| 6,238,344 B1 | 5/2001 | Gamelsky et al. | | 600/437 |
| 6,248,070 B1 | 6/2001 | Kanda et al. | | 600/443 |
| 6,254,539 B1 | 7/2001 | Pang et al. | | 600/443 |
| 6,264,609 B1 | 7/2001 | Herrington et al. | | 600/443 |
| 6,272,469 B1 | 8/2001 | Koritzinsky et al. | | 705/2 |
| 6,277,073 B1 | 8/2001 | Bolorforosh et al. | | 600/437 |
| 6,286,513 B1 * | 9/2001 | Au et al. | | 128/898 |
| 6,302,845 B2 | 10/2001 | Shi et al. | | |
| 6,309,353 B1 | 10/2001 | Cheng et al. | | 600/437 |
| 6,325,758 B1 | 12/2001 | Carol et al. | | 600/439 |
| 6,338,716 B1 | 1/2002 | Hossack et al. | | 600/459 |
| 6,343,936 B1 | 2/2002 | Kaufman et al. | | 434/262 |
| 6,346,124 B1 | 2/2002 | Geiser et al. | | 660/450 |
| 6,350,239 B1 | 2/2002 | Ohad et al. | | 600/437 |
| 6,359,190 B1 | 3/2002 | Ter-Ovanesyan et al. | | 604/361 |
| 6,360,027 B1 | 3/2002 | Hossack et al. | | 382/294 |
| 6,375,616 B1 | 4/2002 | Soferman et al. | | 600/443 |
| 6,400,848 B1 | 6/2002 | Gallagher | | 382/254 |
| 6,402,762 B2 | 6/2002 | Hunter et al. | | 606/130 |
| 6,406,431 B1 | 6/2002 | Barnard et al. | | 600/443 |
| 6,409,665 B1 | 6/2002 | Scott et al. | | 600/437 |
| 6,440,071 B1 | 8/2002 | Slayton et al. | | 600/437 |
| 6,440,072 B1 | 8/2002 | Schuman et al. | | 600/437 |
| 6,443,894 B1 | 9/2002 | Sumanaweera et al. | | 600/443 |
| 6,468,218 B1 | 10/2002 | Chen et al. | | 600/443 |
| 6,485,423 B2 | 11/2002 | Angelsen et al. | | 600/458 |
| 6,491,631 B2 | 12/2002 | Chiao et al. | | 600/443 |
| 6,494,841 B1 | 12/2002 | Thomas et al. | | 600/447 |
| 6,503,204 B1 | 1/2003 | Sumanaweera et al. | | 600/459 |
| 6,511,325 B1 | 1/2003 | Lalka et al. | | 434/272 |
| 6,511,426 B1 | 1/2003 | Hossack et al. | | 600/437 |
| 6,511,427 B1 | 1/2003 | Sliwa, Jr. et al. | | 600/438 |
| 6,515,657 B1 | 2/2003 | Zanelli | | 345/419 |
| 6,524,249 B2 | 2/2003 | Moehring et al. | | 600/438 |
| 6,535,759 B1 | 3/2003 | Epstein et al. | | 600/547 |
| 6,540,679 B2 | 4/2003 | Slayton et al. | | 600/439 |
| 6,544,179 B1 | 4/2003 | Schmiesing et al. | | 600/447 |
| 6,545,678 B1 | 4/2003 | Ohazama | | 345/427 |
| 6,551,246 B1 | 4/2003 | Ustuner et al. | | 600/447 |
| 6,565,512 B1 | 5/2003 | Ganguly et al. | | 600/449 |
| 6,569,097 B1 | 5/2003 | McMorrow et al. | | 600/437 |
| 6,569,101 B2 | 5/2003 | Quistgaard et al. | | 600/459 |
| 6,575,907 B1 | 6/2003 | Soferman et al. | | 600/438 |
| 6,585,647 B1 | 7/2003 | Winder | | 600/437 |
| 6,610,013 B1 | 8/2003 | Fenster et al. | | 600/439 |
| 6,611,141 B1 | 8/2003 | Schulz et al. | | 324/226 |
| 6,622,560 B2 | 9/2003 | Song et al. | | |
| 6,628,743 B1 | 9/2003 | Drummond et al. | | 378/8 |
| 6,643,533 B2 | 11/2003 | Knoplioch et al. | | 600/407 |
| 6,650,927 B1 | 11/2003 | Keidar | | 600/424 |
| 6,676,605 B2 * | 1/2004 | Barnard et al. | | 600/449 |
| 6,682,473 B1 * | 1/2004 | Matsuura et al. | | 600/29 |
| 6,688,177 B2 | 2/2004 | Wiesauer | | 73/618 |
| 6,695,780 B1 | 2/2004 | Nahum et al. | | 600/437 |
| 6,705,993 B2 | 3/2004 | Ebbini et al. | | 600/443 |
| 6,716,175 B2 | 4/2004 | Geiser et al. | | 600/450 |
| 6,752,762 B1 | 6/2004 | DeJong et al. | | 600/458 |
| 6,755,787 B2 | 6/2004 | Hossack et al. | | 600/447 |
| 6,768,811 B2 | 7/2004 | Dinstein et al. | | 382/128 |
| 6,780,152 B2 | 8/2004 | Ustuner et al. | | 600/443 |
| 6,788,620 B2 | 9/2004 | Shiraishi et al. | | 367/152 |
| 6,801,643 B2 | 10/2004 | Pieper | | 382/128 |
| 6,822,374 B1 | 11/2004 | Smith et al. | | 310/334 |
| 6,825,838 B2 | 11/2004 | Smith et al. | | 345/419 |
| 6,831,394 B2 | 12/2004 | Baumgartner et al. | | 310/334 |
| 6,868,594 B2 | 3/2005 | Gururaja | | 29/25.35 |
| 6,884,217 B2 | 4/2005 | McMorrow et al. | | 600/443 |

| | | | |
|---|---|---|---|
| 6,903,813 B2 | 6/2005 | Jung et al. ............... 356/73 |
| 6,905,467 B2 * | 6/2005 | Bradley et al. .......... 600/443 |
| 6,905,468 B2 | 6/2005 | McMorrow et al. ...... 600/443 |
| 6,911,912 B2 * | 6/2005 | Roe ...................... 340/573.1 |
| 6,936,009 B2 | 8/2005 | Venkataramani et al. ... 600/459 |
| 6,939,301 B2 | 9/2005 | Abdelhak ................ 600/437 |
| 6,951,540 B2 | 10/2005 | Ebbini et al. ............ 600/437 |
| 6,954,406 B2 | 10/2005 | Jones ....................... 367/152 |
| 6,961,405 B2 | 11/2005 | Scherch .................... 378/65 |
| 6,962,566 B2 | 11/2005 | Quistgaard et al. ....... 600/437 |
| 6,970,091 B2 * | 11/2005 | Roe ...................... 340/573.1 |
| 7,004,904 B2 * | 2/2006 | Chalana et al. .......... 600/443 |
| 7,025,725 B2 | 4/2006 | Dione et al. ............. 600/443 |
| 7,041,059 B2 * | 5/2006 | Chalana et al. .......... 600/437 |
| 7,042,386 B2 | 5/2006 | Woodford et al. ......... 342/25 |
| 7,087,022 B2 | 8/2006 | Chalana et al. .......... 600/449 |
| 7,141,020 B2 | 11/2006 | Poland et al. ............ 600/447 |
| 7,142,905 B2 | 11/2006 | Slayton et al. ........... 600/427 |
| 7,177,677 B2 | 2/2007 | Kaula et al. ............. 600/546 |
| 7,189,205 B2 | 3/2007 | McMorrow et al. ...... 600/437 |
| 7,215,277 B2 | 5/2007 | Woodford et al. ....... 342/25 F |
| 7,255,678 B2 | 8/2007 | Mehi et al. .............. 600/446 |
| 7,301,636 B2 | 11/2007 | Jung et al. ............... 356/402 |
| 7,382,907 B2 | 6/2008 | Luo et al. ................ 382/128 |
| 7,450,746 B2 | 11/2008 | Yang et al. .............. 382/131 |
| 7,520,857 B2 | 4/2009 | Chalana et al. .......... 600/446 |
| 7,611,466 B2 | 11/2009 | Chalana et al. .......... 600/443 |
| 2001/0031920 A1 | 10/2001 | Kaufman et al. ......... 600/431 |
| 2002/0005071 A1 | 1/2002 | Song et al. .............. 73/606 |
| 2002/0016545 A1 | 2/2002 | Quistgaard et al. ....... 600/437 |
| 2002/0072671 A1 | 6/2002 | Chenal et al. ........... 600/450 |
| 2002/0102023 A1 | 8/2002 | Yamauchi |
| 2002/0133075 A1 | 9/2002 | Abdelhak ............... 600/443 |
| 2002/0147399 A1 | 10/2002 | Mao |
| 2002/0165448 A1 | 11/2002 | Ben-Haim et al. ........ 600/424 |
| 2003/0055336 A1 | 3/2003 | Buck et al. .............. 600/453 |
| 2003/0142587 A1 | 7/2003 | Zeitzew .................... 367/127 |
| 2003/0174872 A1 | 9/2003 | Chalana et al. .......... 382/128 |
| 2003/0181806 A1 | 9/2003 | Medan et al. ............ 600/411 |
| 2003/0216646 A1 | 11/2003 | Angelsen et al. ......... 600/437 |
| 2003/0229281 A1 | 12/2003 | Barnard et al. ........... 600/438 |
| 2004/0006266 A1 | 1/2004 | Ustuner et al. ........... 600/47 |
| 2004/0024302 A1 | 2/2004 | Chalana et al. .......... 600/407 |
| 2004/0034305 A1 | 2/2004 | Song et al. .............. 600/447 |
| 2004/0054280 A1 | 3/2004 | McMorrow et al. ...... 600/437 |
| 2004/0076317 A1 | 4/2004 | Roberts ................... 328/128 |
| 2004/0106869 A1 | 6/2004 | Tepper .................... 600/443 |
| 2004/0127796 A1 | 7/2004 | Chalana |
| 2004/0127797 A1 | 7/2004 | Barnard et al. ........... 600/449 |
| 2004/0267123 A1 | 12/2004 | McMorrow et al. ...... 600/443 |
| 2005/0135707 A1 | 6/2005 | Turek et al. ............. 382/294 |
| 2005/0174324 A1 | 8/2005 | Liberty et al. ........... 345/156 |
| 2005/0193820 A1 | 9/2005 | Sheljaskow et al. ....... 73/649 |
| 2005/0212757 A1 | 9/2005 | Marvit et al. ............ 345/156 |
| 2005/0215896 A1 | 9/2005 | McMorrow et al. ...... 600/437 |
| 2005/0228276 A1 | 10/2005 | He et al. .................. 600/437 |
| 2005/0240126 A1 | 10/2005 | Foley et al. .............. 601/2 |
| 2005/0253806 A1 | 11/2005 | Liberty et al. ........... 345/156 |
| 2006/0025689 A1 | 2/2006 | Chalana et al. .......... 600/456 |
| 2006/0064010 A1 | 3/2006 | Cannon, Jr. et al. ...... 600/434 |
| 2006/0078501 A1 | 4/2006 | Goertz et al. |
| 2006/0079775 A1 | 4/2006 | McMorrow et al. ...... 600/443 |
| 2006/0111633 A1 | 5/2006 | McMorrow et al. ...... 600/437 |
| 2006/0235301 A1 | 10/2006 | Chalana et al. .......... 600/443 |
| 2007/0004983 A1 | 1/2007 | Chalana et al. .......... 600/443 |
| 2007/0232908 A1 | 10/2007 | Wang et al. .............. 600/437 |
| 2007/0276247 A1 | 11/2007 | Chalana et al. .......... 600/447 |
| 2007/0276254 A1 | 11/2007 | Yang et al. .............. 600/463 |
| 2008/0139938 A1 | 6/2008 | Yang et al. .............. 600/445 |
| 2008/0146932 A1 | 6/2008 | Chalana et al. .......... 600/447 |
| 2008/0242985 A1 | 10/2008 | Chalana et al. .......... 600/443 |
| 2008/0249414 A1 | 10/2008 | Yang et al. .............. 600/445 |
| 2008/0262356 A1 | 10/2008 | Chalana et al. .......... 600/447 |
| 2009/0062644 A1 | 3/2009 | McMorrow et al. ...... 600/437 |
| 2009/0088660 A1 | 4/2009 | McMorrow et al. ...... 600/546 |
| 2009/0105585 A1 | 4/2009 | Wang et al. .............. 600/437 |
| 2009/0112089 A1 | 4/2009 | Barnard et al. ........... 600/443 |
| 2009/0264757 A1 | 10/2009 | Yang et al. .............. 600/443 |

FOREIGN PATENT DOCUMENTS

| | | |
|---|---|---|
| EP | 1 030 187 | 8/2000 |
| EP | 1 076 318 | 2/2001 |
| EP | GB2391625 A | 2/2004 |
| JP | 7-171149 | 1/1999 |
| JP | 2000-210286 | 2/2000 |
| JP | 2000-126178 | 5/2000 |
| JP | 2000-126181 | 5/2000 |
| JP | 2000-126182 | 5/2000 |
| WO | 01/35339 | 5/2001 |
| WO | 2009/032778 | 3/2009 |

OTHER PUBLICATIONS

Baker, A., et al.: "Distortion and High-Frequency Generation Due to Nonlinear Propagation of Short Ultrasonic Pulses from a Plane Circular Piston", Journal of Acoustical Society of America, vol. 92, No. 3, pp. 1699-1705, Sep. 1992.

Baker, A., et al., "Prediction of Non-Linear Propagation In Water Due to Diagnostic Medical Ultrasound Equipment", Phys. Med Biol., vol. 36, No. 11, pp. 1457-1464, 1991.

Barentsz et al., "Primary Staging of Urinary Bladder Carcinoma: the Role of MRI and a Comparison with CT," European Radiology vol. 6, pp. 129-133, 1996.

Besl, P., et al., "A Method for Registration of 3-D Shapes," IEEE Transaction on Pattern Analysis and Machine Intelligence, vol. 14, No. 2, pp. 239-256, Feb. 1992.

Birnholz, J., et al., "Amniotic Fluid Accumulation in the First Trimester," American Institute of Ultrasound in Medicine, Journal Ultrasound Medicine, vol. 14, pp. 597-602, 1995.

Bishop, S., et al., "Human Tissue-Temperature Rise During Ultrasound Treatments with the Aquaflex Gel Pad." Journal of Athletic Training, vol. 39, No. 2, pp. 126-131, 2004.

Bouakaz, A., et al., "Noninvasive Bladder Volume Measurements Based on Nonlinear Wave Distortion," Ultrasound in Medicine & Biology, vol. 30, No. 4, pp. 469-476, 2004.

Boyle, P., et al, "Prostate Volume Predicts Outcome of Treatment of Benign Prostatic Hyperplasia with Finasteride: Meta-Analysis of Randomized Clinical Trials," Urology, vol. 48, No. 3, pp. 398-405, 1996.

Cascione, C., et al., "Transabdominal Ultrasound Versus Excretory Urography in Preoperative Evaluation of Patients with Prostatism," The Journal of Urology, vol. 137, pp. 883-885, May 1987.

Chamberlain, P., "Amniotic Fluid Volume: Ultrasound Assessment and Clinical Significance," Seminars in Perinateology, vol. 9, No. 4, pp. 163-167, 1985.

Chamberlain, P. "Ultrasound Evaluation of Amniotic Fluid Volume," American Journal of Obstetrics and Gynaecology, vol. 150, No. 3, pp. 250-254, Oct. 1, 1984.

Cheng, X. et al., "Boundary Extraction Method for Three Dimensional Ultrasonic Echo Imaging Using Fuzzy Reasoning and Relaxation Techniques," IEEE, pp. 1610-1614, 1994.

Christensen, M., et al., "Clinical Manifestations of Benign Prostatic Hyperplasia and Indications for Therapeutic Intervention," Benign Prostatic Hyperplasia, Urologic Clinics of North America, vol. 17, No. 3, pp. 509-516, Aug. 1990.

Crowley, P., et al., "The Value of Ultrasound Measurement of Amniotic Fluid Volume in the Management of Prolonged Pregnancies," British Journal of Obstetrics and Gynaecology, vol. 91, pp. 444-448, May 1984.

Cvitkovic-Kuzmic, A., et al., "Sonographic Measurement of Detrusor Muscle Thickness in Healthy Children," Pedatric Nephrology, vol. 16, pp. 1122-1125, 2001.

Cvitkovic-Kuzmic, A., et al., "Ultrasound Assessment of Detrusor Muscle Thickness in Children with Non-Neuropathic Bladder/Sphincter Dysfunction," European Urology, Vo. 41, pp. 214-219, 2002.

Elliott, P., "Interactive Image Segmentation for Radiation Treatment Planning," IBM Systems Journal, vol. 31, No. 4, pp. 620-634, 1992.

Forbes, F., et al., "Bayesian Morphology: Fast Unsupervised Bayesian Image Analysis," Journal of the American Statistical Association, vol. 94, No. 446, pp. 555-568, Jun. 1999.

Gerald, C., et al., "Applied Numerical Analysis," Fifth Edition, Addison-Wesley Publishing Company, Chapter 3, 'Interplation and Curve Fitting,', pp. 210-287.

Gobbi, D., et al. "Real-Time 3D Ultrasound for Intraoperative Surgical Guidance," 8 pgs.

Gramellini, D., et al., "Sonographic Assessment of Amniotic Fluid Volume Between 11 and 24 Weeks of Gestation: Construction of Reference Intervals Related to Gestational Age," Ultrasound Obstetrics Gynaecology, vol. 17, pp. 410-415, 2001.

Grover, J., et al., "Three-Dimensional Method for Determination of Amniotic Fluid Volume in Intrauterine Pockets," vol. 90, No. 6, pp. 1007-1010, Dec. 1997.

Hakenberg, O., et al., "Bladder Wall Thickness in Normal Adults and Men with Mild Lower Urinary Tract Symptoms and Benign Prostatic Enlargement," Neurourology and Urodynamics, vol. 19, pp. 585-593, 2000.

Hakenberg, O., et al., "The Estimation of Bladder Volume by Sonocystrography," Journal of Urology, vol. 130, No. 2, pp. 249-251, Aug. 1983.

Holmes, J., et al., "Ultrasonic Studies of the Bladder," The Journal of Urology, vol. 91, pp. 654-663, 1967.

Jeng, C., et al., "Amniotic Fluid Index Measurement with the Four-Quadrant Technique During Pregnancy," The Journal of Reproductive Medicine, Inc., vol. 35, No. 7, pp. 674-677, Jul. 1990.

Jequier, S., et al., "Sonographic Measurements of the Normal Bladder Wall in Children," AJR, vol. 149, pp. 563-566, Sep. 1987.

Jong, et al., "Ultrasound Contrast Agents" ISBN 1-85317-858-4 chapter 3 "Contrast-Specific Imaging Methods".

Khullar, V., et al. "A Novel Technique for Measuring Bladder Wall Thickness in Women Using Transvaginal Ultrasound,"Ultrasound Obestetrics and Gyneacology, vol. 4, pp. 220-223, 1994.

Khullar, V., et al., "Ultrasound: a Noninvasive Screening Test for Detrusor Instability," British Journal of Obstetrics and Gynaecology, vol. 103, pp. 904-908, Sep. 1966.

Kojima, M., et al., "Reversible Change of Bladder Hypertrophy Due to Benign Prostatic Hyperplasia After Surgical Relief of Obstruction," The Journal of Urology, vol. 158, pp. 89-93, Jul. 1997.

Kojima, M., et al., "Ultrasonic Estimation of Bladder Weight as a Measure of Bladder Hypertrophy in Men with Infravesical Obstruction: a Preliminary Report," Urology, vol. 47, No. 6, pp. 942-947, 1996.

Krenning, B., et al., "Assessment of Left Ventricular Function by Three-Dimensional Echocardiography," Cardiovascular Ultrasound, 7 pgs., 2003.

Kruczkowski et al., "A Non-Invasive Ultrasonic System to Determine Residual Bladder Volumes", IEEE Engineering in Medicine Biology Society 10th Ann Conf, pp. 1623-1624.

Lea, J., et al., "Registration and Immobilization in Robot-Assisted Surgery," Computer Aided Surgery, vol. 1, No. 2, pp. 80-87, 1995.

Lorensen, W., et al., "Marching Cubes: A High Resolution 3D Surface Construction Algorithm," ACM Siggraph Computer Graphics, vol. 21, No. 4, pp. 163-169, Jul. 1987.

Madsen, F., et al., "Clinical Manifestations of Benign Prostatic Hyperplasia," Advances in Benign Prostatic Hyperplasia, Urologic Clinics of North America, vol. 22, No. 2, pp. 291-298, May 1995.

Magann, E., et al., "Amniotic Fluid Volume Determination," American Journal of Obstetrics and Gynaecology, Vo. 169, No. 2, Part 1, pp. 435-437, 1999.

Magann, E., et al., "Measurement of Amniotic Fluid Volume: Accuracy of Ultrasonography Techniques," American Journal of Obstetrics and Gynaecology, vol. 167, No. 6, pp. 1533-1537, 1992.

Magann, E., et al., "Ultrasound Estimate of Amniotic Fluid Volume: Color Doppler Overdiagnosis of Oligohydramnios," Obstetrics & Gynecology, vol. 98, No. 1, pp. 71-74, Jul. 2001.

Magann, E., et al., "Ultrasound Estamation of Amniotic Fluid Volume Using the Largest Vertical Pocket Containing Umbilical Cord: Measure to or Through the Cord," Ultrasound Obstetrics and Gynecology, vol. 20, pp. 464-467, 2002.

Manieri, C., et al., "The Diagnosis of Bladder Outlet Obstruction in Men by Ultrasound Measurement of Bladder Wall Thickness," The Journal of Urology, vol. 159, 761-765, pp. 761-765, Mar. 1998.

Mann, S., et al., "Novel Technique for Assessing Amniotic Fluid Volume: use of a Three-Dimensional Bladder Scanner," The Journal of Maternal-Fetal Medicine, vol. 9, pp. 308-310, 2000.

Manning, F., et al., "Qualitative Amniotic Fluid Volume Determination by Ultrasound: Antepartum Detection of Intrauterine Growth Retardation," American Journal of Obstetrics and Gynecology, vol. 139, No. 3, pp. 254-258, Feb. 1, 1981.

Martan, A., et al., "Ultrasound Imaging of the Lower Urinary System in Women after Burch Colposuspension," Ultrasound Obstetrics and Gynecology, vol. 17, pp. 58-64, 2001.

Matthews, P. et al., "The Use of Ultrasound in the Investigation of Prostatism," British Journal of Urology, vol. 54, pp. 536-538, 1982.

Merks, E. et al., "Design of a Multilayer Transducer for Acoustic Bladder Volume Assessment," IEEE Transacations on Ultrasonics, Ferroelectrics and Frequency Control, vol. 53, No. 10, pp. 1730-1738, Oct. 2006.

Merks, E., et al., "A KLM-Circuit Model of a Multi-Layer Transducer for Acoustic Bladder Volume Measurements," Ultrasonics, vol. 44, pp. 705-710, Dec. 22, 2006.

Miyashita, H., et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine & Biology, vol. 28, No. 8, pp. 985-990, 2002.

Moore, T., "Superiority of the Four-Quadrant Sum Over the Single-Deepest-Pocket Technique in Ultrasonographic Identification of Abnormal Amniotic Fluid Volumes," American Journal of Obstetrics and Gynecology, vol. 163, No. 5, pp. 762-767, 1990.

Muller, L., et al., "Detrusor Thickness in Healthy Children Assessed by a Standardized Ultrasound Method," The Journal of Urology, vol. 166, pp. 2364-2367, Dec. 2001.

Muller, L., et al., "Standardized Ultrasound Method for Assessing Detrusor Muscle Thickness in Children," The Journal of Urology, vol. 164, pp. 134-138, Jul. 2000.

Myles, T., et al., "Four-Quadrant Assessment of Amniotic Fluid Volume: Distribution's Role in Predicting Fetal Outcome," Journal of Obstetrics and Gynecology, vol. 80, No. 5, pp. 769-774, Nov. 1992.

Naya, Y., et al., "Intraobserver and Interobserver Variance in the Measurement of Ultrasound-Estimated Bladder Weight," Ultrasound in Medicine and Biology, vol. 24, No. 5, pp. 771-773, 1998.

Oelke, M., et al., "Increase in Detrusor Wall Thickness Indicates Bladder Outlet Obstruction (BOO) in Men," World Journal of Urology, vol. 19, pp. 443-452, 2002.

Ohashit, G., et al., "Boundary Estimation for Ultrasonic 3-D Imaging," SPIE vol. 1898 Image Processing, pp. 480-486, 1993.

Oomen, JA, et al., "Towards Assessment of Regional Wall Stress of the Left Ventricle Using 3D Ultrasound Imaging," IEEE Computers in Cardiology, vol. 26, pp. 129-132, 1999.

Phelan, J., et al., Amniotic Fluid Volume Assessment with the Four-Quadrant Technique at 36-42 Weeks' Gestation, The Journal of Reproductive Medicine, vol. 32, No. 7, pp. 540-542, Jul. 1987.

Rutherford, S., et al., "The Four-Quadrant Assessment of Amniotic Fluid Volume: An Adjunct to Antepartum Fetal Heart Rate Testing," Journal of Obstetrics and Gynecology, vol. 70, No. 3, Part 1, pp. 353-356, Sep. 1987.

Sagiv, C., et al., "Application of a Semiautomatic Boundary Detection Algorithm for the Assessment of Amniotic Fluid Quantity Form Ultrasound Images," Ultrasound in Medicine and Biology, vol. 25, No. 4, pp. 515-526, 1999.

Sahin, B., et al., "Estimation of the Amniotic Fluid Volume Using the Cavalieri Method on Ultrasound Images," International Journal of Gynecology and Obstetrics, vol. 82, pp. 25-30, 2003.

Santilli, J., et al., "Diagnosis and Treatment of Abdominal Aortic Aneurysms," American Family Physician, vol. 56, No. 4, pp. 1081-1090, Sep. 1997.

Scheinerman, E., "Invitation to Dynamical Systems," Chapter 5, 'Fractals,' Prentice Hall pp. 231-315, 1996.

Schiff, E., et al., "Standardized Measurement of Amniotic Fluid Volume by Correlation of Sonography with Dye Dilution Technique," Obestetrics and Gynecology, vol. 76, No. 1, pp. 44-46, Jul. 1990.

Schrimmer, D., et al., "Sonographic Evaluation of Amniotic Fluid Volume," Clinical Obstetrics and Gynecology, vol. 45, No. 4, pp. 1026-1029, 2002.

Sepulveda W., et al., "Direct Volume Measurement at Midtrimester Amnioinfusion in Relation to Ultrasonographic Indexes of Amniotic Fluid Volume," American Journal of Obstetrics and Gynecology, vol. 170, No. 4, pp. 1160-1163, Apr. 1994.

Shiota, T., et al., "Real-time Three-Dimensional Echocardiography for Determining Right Ventricular Stroke Volume in an Animal Model of Chronic Right Ventricular Volume Overload," Circulation Journal of the American Heart Association, vol. 97, pp. 1897-1900, 1998.

Stangenberg, M., et al., "Amniotic Fluid Volumes in Pregnant Diabetics During the Last Trimester," Acta Obstetrics Gynecology Scand, vol. 61, pp. 313-316, 1982.

Szabo, T., et al., "Effects of Nonlinearity on the Estimation of In Situ Values of Acoustic Output Parameters," Journal of Ultrasound in Medicine, American Institute of of Ultrasound in Medicine, vol. 18, No. 1, pp. 33-41, 1999.

Weissman, A., et al., "Sonographic Measurement of Amniotic Fluid Volume in the First Trimester of Pregnancy," American Institute of Ultrasound in Medicine, vol. 15, pp. 771-774, 1996.

Examiner to Applicant Correspondence—Prosecution History of co-pending application by Gerald McMorrow, U.S. Appl. No. 11/010,539, filed Dec. 13, 2004, entitled "Instantaneous Ultrasonic Echo Measurement of Bladder Volume with a Limited Number of Ultrasound Beams."

* cited by examiner

Figure 2. Various, filling dependent measurement configurations.

INSTANTANEOUS ULTRASONIC MEASUREMENT OF BLADDER VOLUME

The present invention relates to methods and apparatus for the measurement of volume of a fluid filled cavity in a human or animal body, such as a bladder, using ultrasound techniques.

TECHNICAL FIELD

This invention concerns an apparatus which, in a first version, with a limited number of fixed ultrasound transducers with narrow sound beams oriented in well defined directions, automatically determines the volume of the human bladder without assumption of any geometrical bladder shape, where volume is calculated by (Height×Depth×K) and the empirically measured K factor varies with bladder filling degree, which in turn is indicated by the number of ultrasonic beams that intercept the filled bladder. In this first version, standard echographic technique is used where short ultrasound pulses are transmitted at fundamental frequency and the echo travel time is used to calculate distance.

In a second version, with a wide ultrasound beam, pulses are transmitted at fundamental frequency. Due to the wide sound beam this beam encompasses a large part of the volume of a possibly filled bladder. Echo signals from a large distance W, where W is the average distance from the transducer in dorsal direction to a point beyond the posterior wall of an average filled bladder, are analyzed for higher harmonic contents. Non-linear behavior will increase with depth and particularly be stimulated by presence of urine. Attenuation of returned echo signals from a large distance will be considerably less in the presence of urine. A combination of these two effects will favor presence of higher harmonics as compared to the presence of the fundamental frequency in the return signal. With this information urine quantity or a critical urine filling level of the bladder can be established.

In a third version a combination of a narrow ultrasound beam for detection of the posterior bladder wall distance W with the wide acoustic beam approach for subsequent measurement of urine filling of the bladder is described.

BACKGROUND OF THE INVENTION

It is well known that bladder dysfunction is associated with a number of clinical conditions requiring treatment. In many of these cases it is important to accurately determine the volume of the bladder. Under other conditions is such as post-operative recovery, where there is temporary loss of bladder sensation and/or loss of the normal voiding mechanism too much distention of the bladder has to be avoided. Under those conditions voiding by catheter introduction is carried out. However, serious disadvantages to unnecessary catheterization range from the uncomfortable situation for the patient to serious possibilities of infection. Thus, a non-invasive quick measurement of bladder volume, with the patient usually in the supine position, is indicated. Sometimes the accurate determination of volume is indicated; sometimes however an indication is sufficient. Questions that may be asked are for instance: after voiding: "is there still too much urine left?"; or after surgery "is the bladder filling above a certain level so that voiding is necessary?"

Non-invasive procedures for bladder volume estimation are known, but are either unreliable or expensive or have some other significant disadvantages. Palpation and auscultatory percussion are known to be unreliable, while radiography and dye-excretion techniques are known to be similarly inaccurate. For assessing bladder volume, catheterization remains the "gold standard". However, it is invasive, painful and might produce traumas or infections.

SUBJECT

The described technique concerns measurement of urine volume in the human bladder with the use of pulsed ultrasound with a limited number of ultrasound transducers.

In a first version a limited number of transducers are mounted in a transducer assembly. The assembly is positioned non-invasively at the body skin over the position of the bladder with the patient in a supine position. For acoustic contact a coupling gel may be used. Each ultrasound transducer in the assembly transmits and receives the ultrasound signal in a narrow beam through the contact plane. During the measurement the transducers are used in a certain succession. All transducers have been mounted in the assembly such that in transmission and reception successively the beams penetrate the area of the bladder in approximately the sagittal cross sectional plane. The sagittal plane is here defined as antero-posterior plane of the body. One transducer beam direction is dorsal with in addition at least one transducer beam in the dorsal-caudal and one transducer beam in the dorsal-cranial direction. The volume is calculated on the basis of two bladder measurements defined in the sagittal plane as Depth (D) and Height (H). These measurements are derived on the basis of echo travel time from echoes originating at the anterior and posterior bladder wall. Depth is in principle a measurement in dorsal direction. Height is a measurement approximately in the cranial direction. The volume is calculated depending on the specific, filling dependent, measurement configuration following the formula D×H×K. Where K is an empirically measured, filling configuration dependant, correction factor. Beam directions and examples for D and H are illustrated in FIGS. 1 and 2.

In a second version of the described technique a single wide beam ultrasound transducer is positioned non-invasively at the body skin over the location of the bladder. The wide beam can be created by the curved surface of the transducer or by a flat acoustically active surface of for instance a disk shaped transducer supplied with a curved lens. Ultrasonic signals are transmitted and received in the wide, cone like, ultrasound beam and propagation is approximately spherical. Similar to the above described method a pulsed echo signal is transmitted at fundamental ultrasonic frequency. In this second version of the described technique echo data are analyzed as originating from a distance beyond the average position of the posterior (filled) bladder wall. The received echo signal will contain information over almost the entire bladder as encompassed by the wide ultrasound beam. Due to non-linearity, higher harmonic components will build up during propagation and thus be reflected in the returning echo. Compared to propagation through normal tissue, the presence of higher harmonics in the signal is greatly stimulated when propagating through urine. Analyses of presence of higher harmonic components in relation to the fundamental frequency is used for indication of presence of urine in the bladder. Neutralizing patient variation as to obesity etc can also be accomplished by comparing echo signals received from sequentially transmitted pulses at low transmit power (linear propagation only) and pulse transmission at high power (enhancing non-linearity).

STATE OF THE ART

Non-invasive bladder volume measurement techniques with ultrasound echography have been described in the art. In principle, echography measures distance based on echo travel time. Early echo techniques did use a single ultrasound transducer and echo presentation was recorded as echo amplitude versus depth. West, K A: "Sonocystography: A method for measuring residual urine", Scand J Urol Nephrol 1: pp68-70, 1967 describes the subsequent use of some discrete beam directions. He does not have a separate transducer for each beam direction. His method is only qualitative, not instantaneous, and based on distance measurement to the dorsal posterior bladder wall. His method is not adjusted to specific, filling dependent, measuring configurations. A relation between the difference in echo travel time between echoes from the posterior an anterior bladder wall and the independently measured bladder volume has been reported by Holmes, J H: "Ultrasonic studies of the bladder", J Urology, Vol 97, pp. 654-663. His described volume measurement method is exclusively based on bladder depth measurement. Since the bladder changes in shape when filling, a single distance measurement is not precise enough to predict the entire bladder volume. No filling dependent measurement configuration is used.

Diagnostic ultrasound is today well known for real-time cross-sectional imaging of human organs. For cross-sectional imaging the sound beam has to be swept electronically or mechanically through the cross section to be imaged. Echoes are presented as intensity modulated dot on the display. The instruments are costly and require a skilled operator. Volume is sometimes calculated based on bladder contours obtained in two orthogonal planes with a geometric assumption of bladder shape. For 3-dimensional or volumetric echography the sound beam has to be swept through the entire organ. This further increases complexity, acquisition time of the data, and costs of the instrument.

Hakenberg et al: "The Estimation of Bladder Volume by Sonocystography", J Urol, Vol 130, pp249-251, have reported a simple method that is based on measuring the diameters obtained in a cross sectional image in the midline sagittal bladder plane only. The bladder volume has been related to bladder Height and Depth as follows: Volume is Height× Depth×6.6 ml. This formula showed a good correlation coefficient (r=0.942) with a relatively large average error of 30.1%. For this approach a two-dimensional imaging apparatus was required. The used apparatus is complex and is different from the method described in this application. It does not use a single wide beam transducer or a limited number of fixed transducers in an assembly or a combination of this.

An ultrasound apparatus for determining the bladder volume is shown in U.S. Pat. No. 4,926,871 in the name of Dipankar Ganguly et al. In this text, a number of possibilities are mentioned, amongst which a scan head embodiment referred to as a sparse linear array with transducers mounted at predetermined angles with sound beams pointing towards the same position. The volume is calculated according to a geometric model. In the claims an apparatus is described, involving an automatic calculation of bladder volume from ultrasound measurements in a first and second plane, which are substantially orthogonal to each other. Sound beams are deflected by a stepper motor. It requires a skilled operator to manipulate the scan head in a particular way to obtain the ultrasound measurements. For the volume calculation method described in this application no use is made of any geometrical model of the bladder, whereas only a limited number of sound beams approximately in the sagittal plane, or a single wide beam is used.

Volume measurement based on echographic sampling of the bladder with a hand guided transducer mounted in a panthograph has been described by Kniczkowski et al: "A non-invasive ultrasonic system to determine residual bladder volume", IEEE Eng in Medicine & Biology Soc 10th Ann Conf, pp1623-1624. The sampling covers the entire bladder, follows a given pattern and is not limited to a single or two cross sections of the bladder. For the calculation he needs data from many beam directions. The acquisition procedure is time consuming and thus no instantaneous volume measurement results. The method described in this application is based on use of a single, wide beam or the use of a limited number of mutually fixed sound beams directions with instantaneous volume indication.

The hand steered transducer guiding for recording of echo data from the bladder has subsequently gained in acquisition speed by introduction of constructions whereby the transducer, and thus the beam, was mechanically swept. This nevertheless still requires an acquisition time equivalent to full acquisition procedure and thus does not yield an instantaneous display of volume. No instantaneous feedback on optimal positioning is thus available. An example of such methods is the Bladderscan. In the Bladderscan Technology (registered trademark of Diagnostic Ultrasound Corporation) bladder volume is measured by interrogating a three-dimensional region containing the bladder and then performing image detection on the ultrasound signals returned from the region insonated. The three dimensional scan is achieved by performing twelve planar scans rotated by mechanically sweeping a transducer through a 97 degree arc in steps of 1.9 degrees. The three dimensional scanning requirement makes this instrument complex. It can not be compared with the simple approach described in this application.

Yet another ultrasound method "System for estimating bladder volume" is described by Ganguly et al in U.S. Pat. No. 5,964,710 dated Oct. 12, 1999. This method is based on bladder wall contour detection with echographically obtained data in a plurality of planes which subdivide the bladder. In each single plane of the plurality of planes a number of N transducers are positioned on a line to produce N ultrasound beams to measure at N positions the distance from front to back wall in the selected plan. From this the surface is derived. This procedure is repeated in the other planes as well. The volume is calculated from the weighted sum of the plurality of planes. In Ganguly's method the entire border of the bladder is echographically sampled in 3 dimensions. His method differs strongly from the method described in this application whereby only a single wide beam is used or a limited number of mutually fixed sound directions are used in approximately a sagittal plane with a filling dependent measurement configuration.

U.S. Pat. No. 6,359,190 describes a device for measuring the volume of a body cavity, such as a bladder or rectum, using ultrasound. The device is strapped to the body or incorporated into a garment such as a nappy or trainer pant. The device includes several transducers each aimed at a different region of the subject's bladder (a) to ensure that at least one ultrasound beam crosses the bladder despite variations in the way that the device has been positioned on the body, and (b) to enable the transducer with the strongest signal output to be used. An alarm signal may be output when the bladder reaches a predetermined threshold volume.

An important parameter for assessing bladder volume if this volume has to be derived from a limited number of beams or planes is the knowledge of bladder shape and position which can drastically vary with age, gender, filling degree and disease. In the adult patient the empty bladder has the shape of a triangular prism and is located behind the pubis. When it is progressively filled, there is first a distention of the bladder depth followed by an expansion of the bladder height. The bladder shape is complex and can not be represented by a single geometrical formula such as ellipsoid, sphere etc. This explains the large error that several studies obtained when a single geometric model was used. However there exists a correlation between the bladder height and the bladder widening with progressive filling.

In the first approach of the present invention an instrument is described which allows assessment of bladder volume by using only a few ultrasound beams appropriately oriented in approximately the sagittal plane. The narrow sound beams in principle diverge relative to each other. This allows covering a wide range of filling degrees of the bladder, from almost empty, when the bladder is located behind the pubis, to a full bladder that causes a substantial bladder height (See FIGS. 1 and 2). From each beam can be established, by detection of the posterior bladder wall echo, if this beam does pass a filled bladder. From the knowledge of all beams that do pass the filled bladder the appropriate filling or measurement configuration follows. The acoustic beams are positioned in such a way that the Depth D and Height H of the bladder can be estimated for the specific measurement configuration. The volume of urine is then computed from an empirical formula D×H×K that does not depend on any geometric model. K is a known, empirically established correction factor which is specific for each measurement configuration and has been established by calibrated bladder measurements on a prior series of patients. The accuracy of the first approach is thus based on an a prior known correction factor which is related to a specific filling degree, which in turn depends on the number of beams that intercept the filled bladder.

A second version of the instrument is based on the measurement of the presence of higher harmonics in the echo signal. For this approach the echo signal from a depth greater than the distance from the transducer to the posterior bladder wall must be analyzed. For a filled bladder in adults in a supine position, this depth W would be approximately 12 cm.

It is known that when sound pulses are transmitted at a fundamental frequency, higher harmonics of this fundamental frequency may be present in the received echographic signal. Non-linear distortion increases with distance, insonifying ultrasound energy and frequency. Attenuation diminishes the ultrasound amplitude with increasing propagation distance and reduces the higher harmonic energy. Since attenuation of the ultrasound signal in urine is low compared to tissue and non-linear distortion in urine is large compared to tissue it results that urine is very different from tissue in its ability to generate higher harmonics. We have measured the presence of higher harmonics in the echo signal from 12 cm depth when the bladder was filled. With an empty bladder the echoes obtained from the same depth did not contain higher harmonics.

The interest of higher harmonic signals in the ultrasound technique stems from echo contrast technology. Echo contrast material contains coated gas containing micro bubbles suspended in a fluid. These bubbles can create higher harmonic components in the echo signal due to non-linearity. This is used to indicate presence of contrast on the diagnostic image. A wide variety of pulse techniques is used to stimulate echographic visibility of contrast. These include multi pulse procedures, multi frequency procedures, power Doppler imaging, pulse coding, pulse inversion and other imaging methods. A survey is documented in "Ultrasound Contrast Agents" ISBN 1-85317-858-4 chapter 3 "Contrast-specific imaging methods" by de Jong et al. With a single transducer with wide sound beam, such as results with a curved acoustic element or a flat, disk shaped transducer plus curved lens, the propagating sound beam would encompass the entire bladder. The transducer must be designed to optimally transmit the fundamental ultrasound frequency and at the same time be capable to receive fundamental and higher harmonic echo signals. Broadband piezo-electric ceramic transducers have been described as well as combination transducers using ceramic in transmission and PVDF material in reception. In transmission a single or multi pulse procedure can be followed. If the returned echo signal with such a method would, in relation to the fundamental echo signal, be analyzed for the presence of higher harmonics, the presence of a certain level of bladder filling or the volume of urine can be established.

EP 0271214 describes an ultrasonic device for monitoring the volume of fluid in the human bladder by using reflected ultrasound signals to determine not only the position of the bladder back wall but also energy returned from the bladder back wall. EP '214 proposes that after bladder filling to approximately 60% capacity, the distance between the back wall and the front wall of the bladder stops increasing. However, additional reverberation in the back wall provides an increase in energy in the reflected signal which can be used to determine further increases in bladder volume.

DESCRIPTION OF THE DRAWINGS

In FIG. 1 the patient's leg is indicated by 4.

A) DETAILED DESCRIPTION OF THE FIRST METHOD

The first method describes a simple device that allows the assessment of bladder 23 volume, using only a few beams appropriately oriented. Under the assumption that there exists a correlation between the bladder height and width, a simple approach has been developed. It consists of a limited number of acoustic beams positioned in such a way that the depth D and the height H of the bladder could be estimated in approximately a single sagittal plane. The volume of urine is then computed from an empirical formula that does not assume any geometric model.

Figure 5:
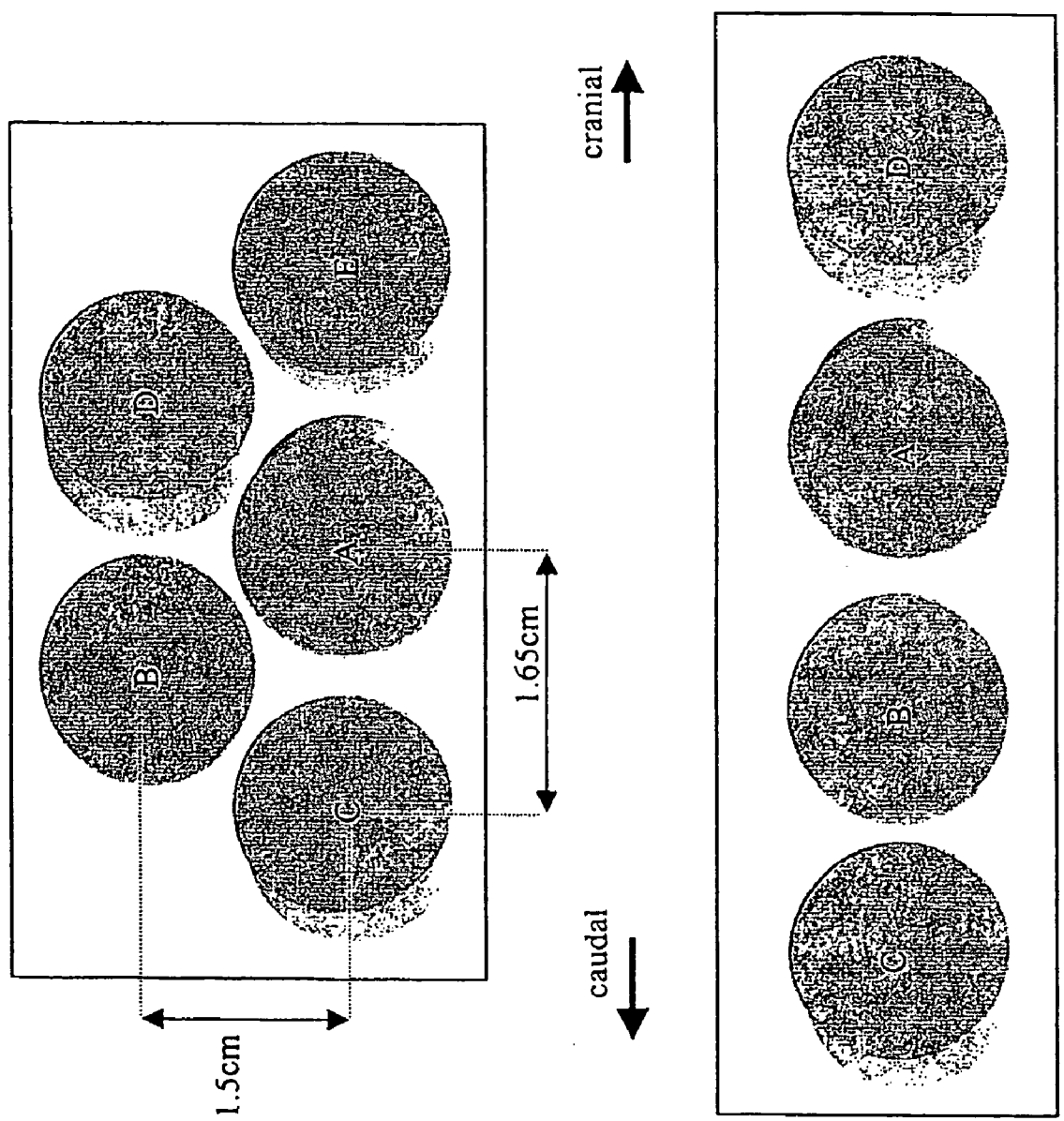
FIG. 5. Illustrates a top view of five disk shaped transducers in a possible transducer assembly. The distance between transducers B, D and C, A, E and their positioning is such that all sound beams can be assumed to be in approximately a sagittal cross section through the bladder. Yet another transducer assembly with 4 transducers in a row is also illustrated.
Figure 6:
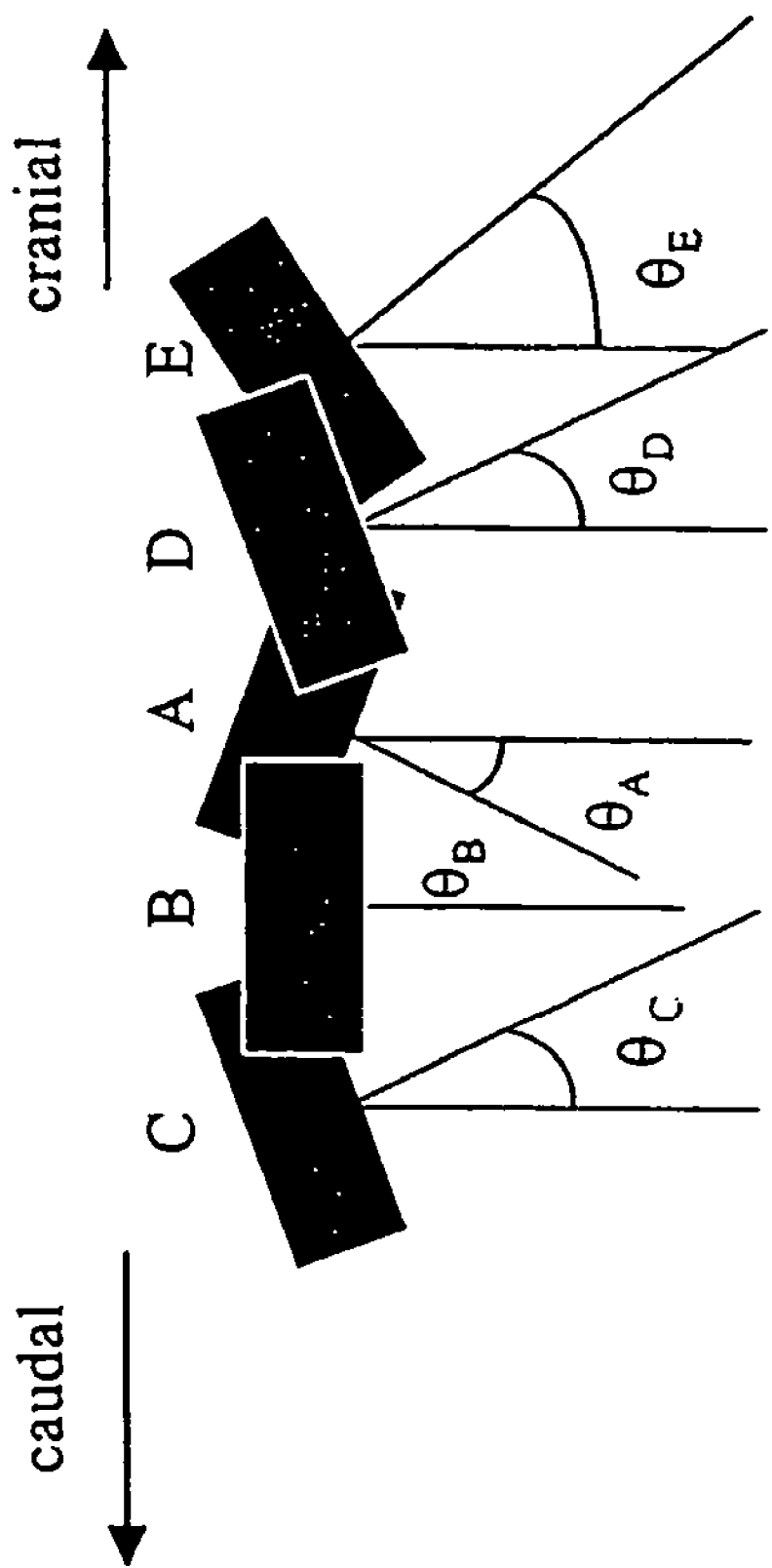
FIG. 6. Illustrates a cross sectional view showing in the length direction a possible transducer and related sound beam orientation when five single transducers are used.

In operation of the apparatus of the present invention, the transducer assembly 1 is placed on the abdomen of the patient in the supine position, just above the symphysis pubis 2. We are presenting a particular configuration of the assembly 1. Nevertheless, various configurations can be derived from this model and several modifications could be achieved (number of transducers, position, orientation, etc. . . . ) without departing from the initial ideas. The device proposed as an example is composed of five disc shaped transducers A, B, C, D and E (focused or non-focused) positioned in the assembly at predetermined distance from each other (FIG. 5, top panel) and oriented at predetermined angles $\theta_A$, $\theta_B$, $\theta_C$, $\theta_D$ and $\theta_E$ (FIG. 6). Referring to FIG. 5 (top panel), it appears that the transducers A, B, C, D and E are oriented in two different planes. The distance between these two planes is small compared to the bladder 3 size and thus we can assume that the information received from each transducer represent the characteristics of approximately a single sagittal or anteroposterior plane. The orientation of each beam has been determined from the knowledge of the bladder 3 position and shape when it is filling up as measured in a patient series. The first beam of the transducer assembly 1 (soundbeam from transducer A) is oriented in such a way that it reaches the bottom of the bladder, passing just above the symphysis pubis 2. The remaining beams are positioned for successively intercepting the bladder 3 when it expands with increasing filling degree.

Computation of the Depth D and Height 5: Depending on the number of beams that are intercepting the bladder 3 and on the geometrical configuration of the transducer assembly (1), the distances H and D are determined by different mathematical procedures. For most measurement configurations the depth D of the bladder is determined by the distance between echoes derived from front and back wall of the bladder estimated from Transducer B.

Figure 1:
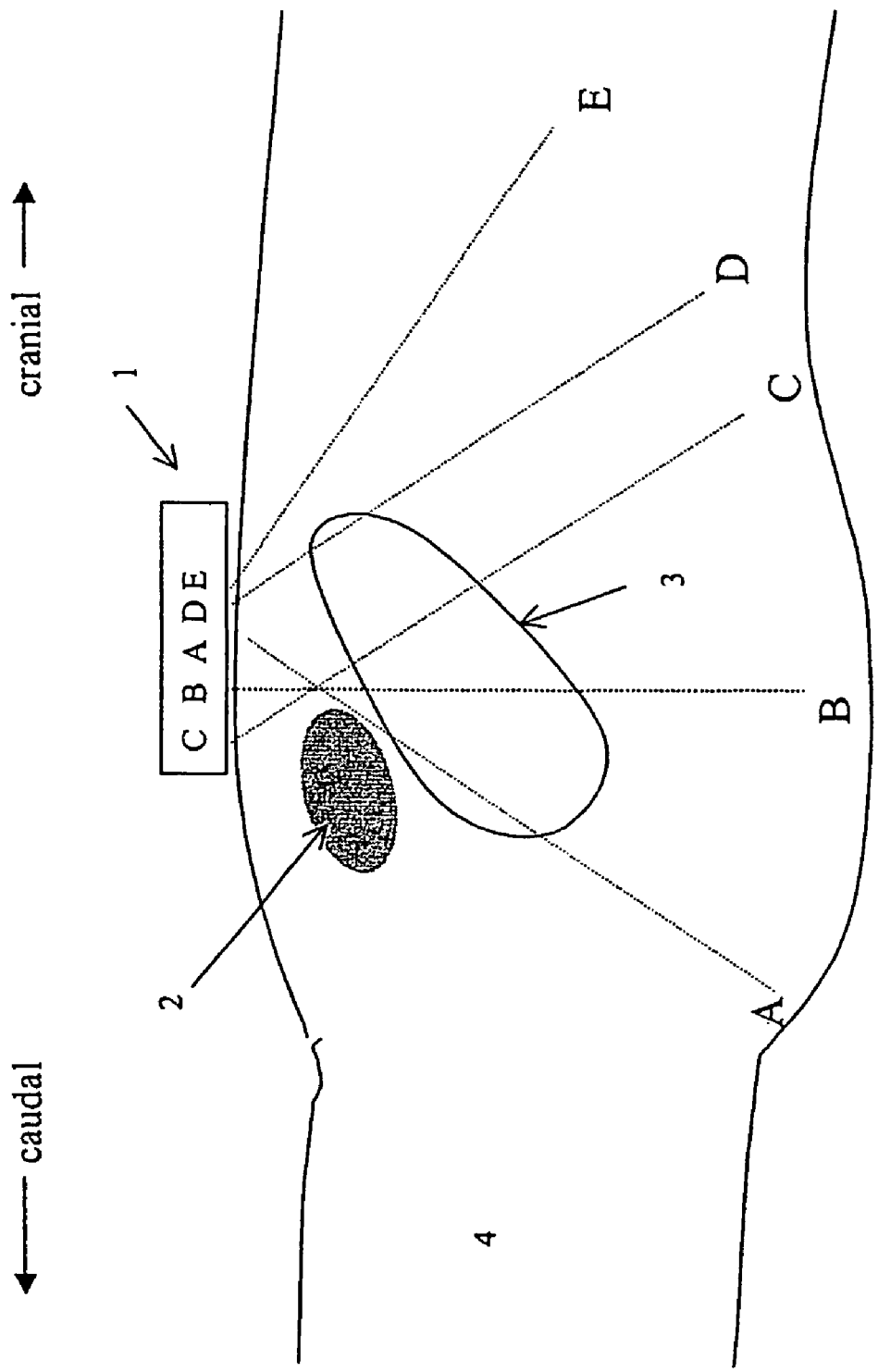
FIG. 1 Illustrates a sagittal (anteroposterior) cross sectional plane of a patient in supine position where a transducer assembly 1 with transducers A, B, C, D and E, is positioned on the abdominal wall just above the Symphysis Pubis 2 and the ultrasound beams are indicated to cross the area of the partially filled bladder 3. From the transducer assembly, the sound beam A intercepts the bladder area in dorso-caudal direction, soundbeam B intercepts the bladder in dorsal direction and sound beams C, D, and E respectively in dorso-cranial direction.
Figure 2:
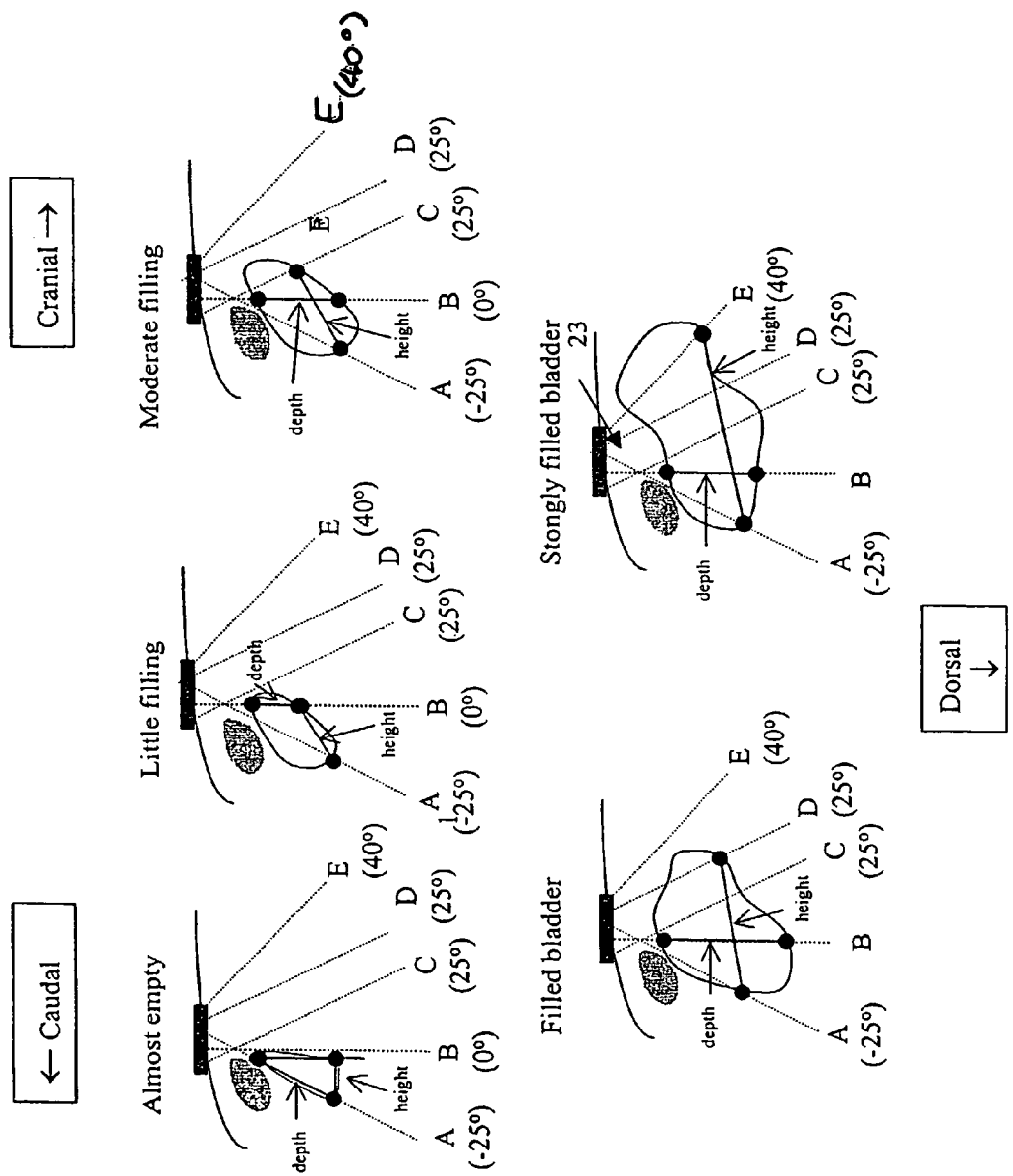
FIG. 2 Illustrates various bladder filling stages from an almost empty bladder to a strongly filled bladder and the corresponding measurement configurations. Depth D and Height H have been defined for each filling situation as indicated and are calculated from detected bladder wall echoes taking the specific measurement configuration into account. For each measurement configuration a specific Depth D and Height H is defined.
Figure 3:
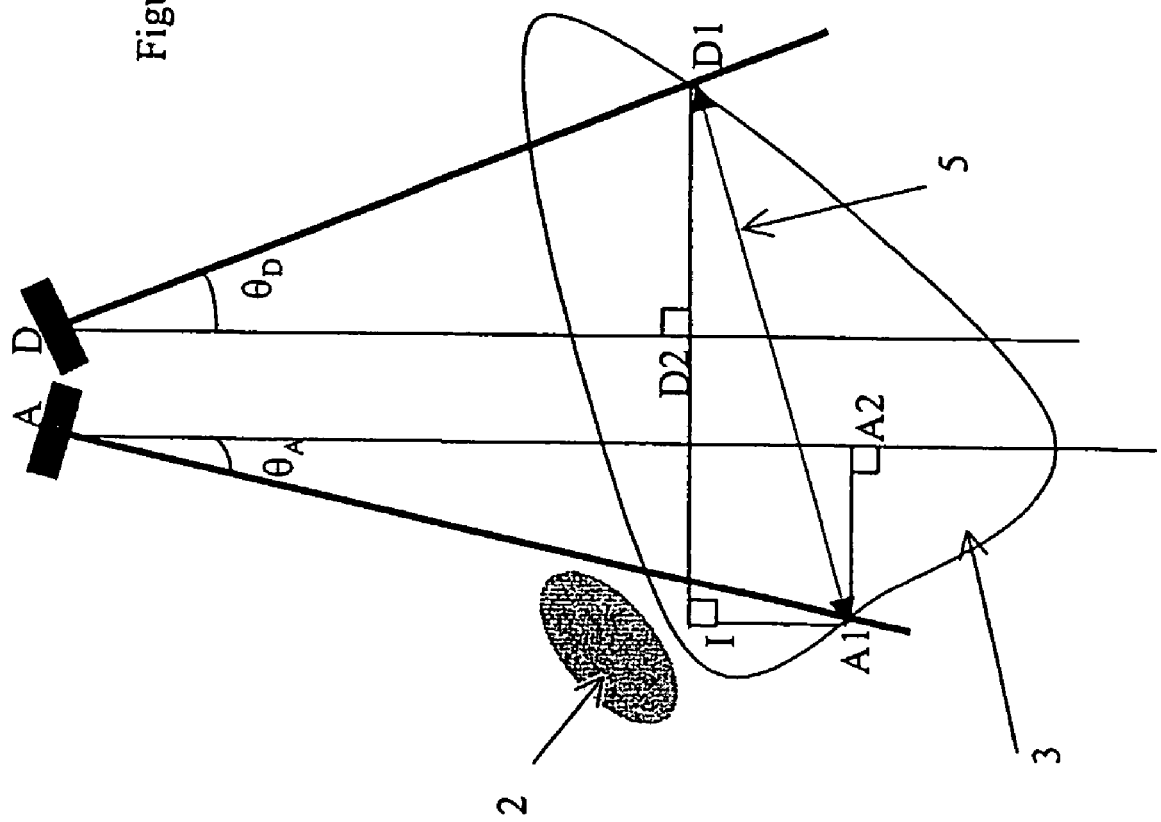
FIG. 3. Illustrates, by way of example for a transducer assembly with five transducers (here only A and D, necessary for calculation of H are shown), the calculation of Height H (5) in the measurement configuration when bladder posterior wall echoes are detected originating from sound beam A, B, C and D. This is the "filled bladder" measurement configuration shown in FIG. 2. Apparently no posterior wall echoes are detected in sound beam E because the bladder filling is not yet in a strongly filled stage and thus beam E does not intercept the bladder. Depth D is derived from beam B (not shown in FIG. 3).

The Height H (5) calculation in the specific measurement configuration (here we selected as an example the "filled bladder" configuration of FIG. 2) when posterior bladder wall echoes are detected in signals obtained in beam A, B, C, and D, but not in beam E is illustrated in FIG. 3. For the other filling geometries the height is calculated in a corresponding way. The mathematical procedure is as follows:

$$\cos\theta_A = \frac{[AA2]}{[AA1]} \Rightarrow [AA2] = \cos\theta_A \cdot [AA1] \quad (1)$$

$$\sin\theta_A = \frac{[A1A2]}{[AA1]} \Rightarrow [A1A2] = \sin\theta_A \cdot [AA1] \quad (2)$$

$$\cos\theta_D = \frac{[DD2]}{[DD1]} \Rightarrow [DD2] = \cos\theta_D \cdot [DD1] \quad (3)$$

$$\sin\theta_D = \frac{[D1D2]}{[DD1]} \Rightarrow [D1D2] = \sin\theta_D \cdot [DD1] \quad (4)$$

$$[A1I] = |[AA2] - [DD2]| \quad (5)$$

$$[ID1] = [D1D2] + [A1A2] + [AD] \quad (6)$$

$$\Rightarrow \text{Height} = [A1D1] = \sqrt{[A1I]^2 + [ID1]^2} \quad (7)$$

Volume computation: The volume of urine is correlated to the bladder diameter (Height 27 and Depth 26) by the empirical formulae:

Height*Depth*K where K is a correction factor. Depending on the number of beams that allow the determination of the bladder dimensions (from 1 to 5) and others parameters such as the age, the gender, the correction factor is different. For a given situation (parameters other than number of beam are fixed), the correction factors K1, K2, K3, K4 and K5 are optimized using linear regression analysis.

Figure 4:
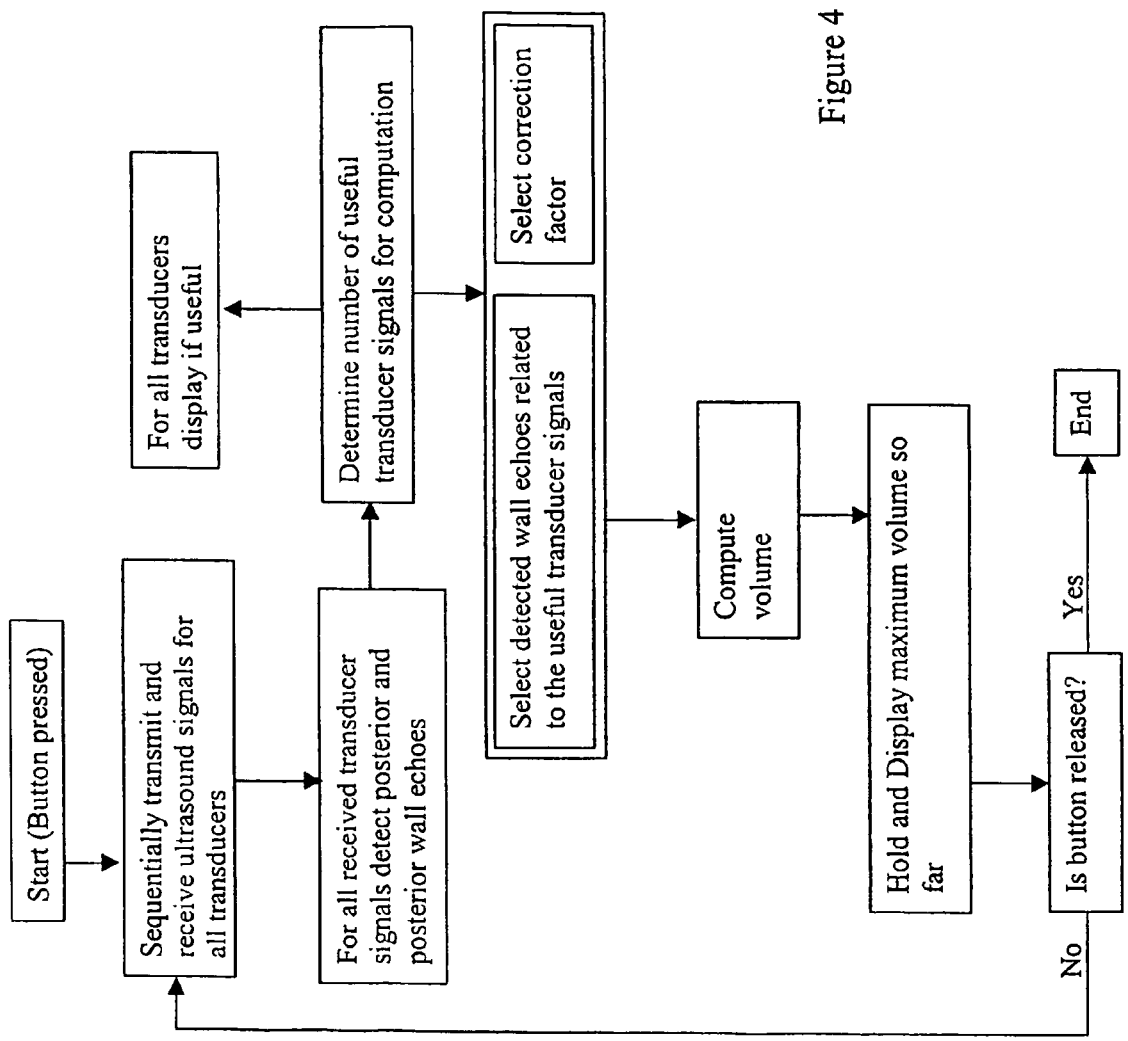
FIG. 4 Represents a flow chart of the actions of the principal hardware components. In this block diagram a "useful" transducer signal occurs when bladder wall echoes are detectable in its sound beam.

The process executed by the hardware is illustrated in the flow chart of FIG. 4.

After positioning the transducer assembly correctly over the bladder area the measurement procedure is started by pressing the start button which during the (short) measurement procedure remains depressed. Subsequently the transducers are activated for transmission of ultrasound pulses and reception of echoes and possible detection of bladder wall echoes in a specific order. Thereafter it is established, when a clear posterior bladder wall echo is detected, which ultrasound beams, this we call here the beams of "useful" transducers, penetrate the filled bladder. From this, the filling situation or measurement geometry is established. As a result the proper correction factor can be selected. After calculation of the volume the value is stored in memory and displayed. During the measurement procedure the transducer assembly is slightly moved and memory data are refreshed if a larger volume is measured. The highest value will correspond with the correct bladder volume. This is displayed.

In a general aspect, therefore, the apparatus may use beam information comprising at least: angle of incidence (known from the transducer mounting angle), spatial position (known from the transducer position in the array) and echo travel time (deduced from the reflected beam). Other beam parameters or information from reflected beams may also be used in accordance with known ultrasound techniques, such as frequency, pulse rate etc.

For determining body cavity and height, the apparatus may select only beams corresponding to those that have intercepted the fluid filled body cavity.

The arrangements described in connection with FIGS. 1 to 6 illustrate use of five transducers. This configuration was selected in order to achieve a selected degree of accuracy of measurement over a complete expected range of total volumes in a human adult. In the preferred configuration, accuracy of measurement of the order of ±100 ml over a range encompassing a bladder fill level from 0 to approximately 800 ml has been exhibited. It will be understood that a smaller number of transducers could be used when either the desired measurement accuracy can be reduced, or when the total fill range covered can be reduced.

For example, using just three transducers, it has been shown to be possible to cover a fill range of 0 to approximately 500 ml with an accuracy of ±100 ml. Similarly, four transducers has been shown to cover a range 0 to approximately 700 ml, and two transducers, a range of 0 to approximately 300 ml.

Such configurations can be used when it is only necessary to indicate gross ranges of bladder filling, or to indicate a clinically important threshold fill level.

In other embodiments, the apparatus may be provided with an input device such as a keypad or computer interface so that the user can enter patient information, such as gender, weight and age. This information can then be used to ensure correct selection of an available correction factor, K, from a memory of the apparatus.

The apparatus may also be provided with means for inputting calibration data, such as absolute measurements of bladder fill level separately deduced from conventional measurements. These can be stored by the apparatus and used to optimise stored K values as part of an iterative, 'self-learning' process. In other words, the apparatus may incorporate an algorithm for automatically adjusting predetermined correction factors stored therein based on calibration data entered into the machine for comparison with measurement data taken by the apparatus.

The apparatus may also comprise a means for indicating correct caudal-cranial positioning of the transducer array on the body over the bladder. For example, in a normal measurement as suggested in FIG. 1, it is expected that at least transducers A, B and C will indicate a bladder present condition, whereas transducers D and E might, or might not indicate bladder present, according to the bladder fill level. In the event that, for example, no signal is indicated by A, or by A and B, but signal is indicated by D or D and E, then it can be deduced that the transducer assembly is positioned too far in the cranial direction. This could be indicated on the display of the device.

In summary, the described first method differs greatly from known other apparatus:

1) The device is composed of a limited number of static single element transducers;
2) The arrangement of the transducer is not similar to the arrangement of a linear array;
3) The transducers are oriented towards the bladder with specific angles allowing the estimation of the urine volume over a wide range of volumes;
4) The method for automatic volume computation does not assume any geometrical model for the bladder shape;
5) It is valid for any bladder shape since the volume is computed with an empirical formula for various filling ranges;
6) It is not based only on the measurement of distances between the front and back wall or area in different planes;
7) It uses an automatic detection of the bladder height and depth depending on the number of beams that intercept the bladder;
8) It optimizes the correction factor depending on the degree of filling (or other factors, such as age, gender, weight, that may influence the calculations);
9) The device includes a closed loop to easily find the optimal position;
10) The optimal position corresponds to the largest volume computed;
11) The device works instantaneously.

B) DETAILED DESCRIPTION OF THE SECOND METHOD

The second version of the device is based on a different principle. The approach consists of using a single acoustic beam with a very wide width such that it encloses approximately the entire volume of the bladder when it is filled up. Such a wide beam width can be obtained using a single element transducer with a defocusing lens as drawn in FIG. 7 or a curved single element transducer.

Figure 7:
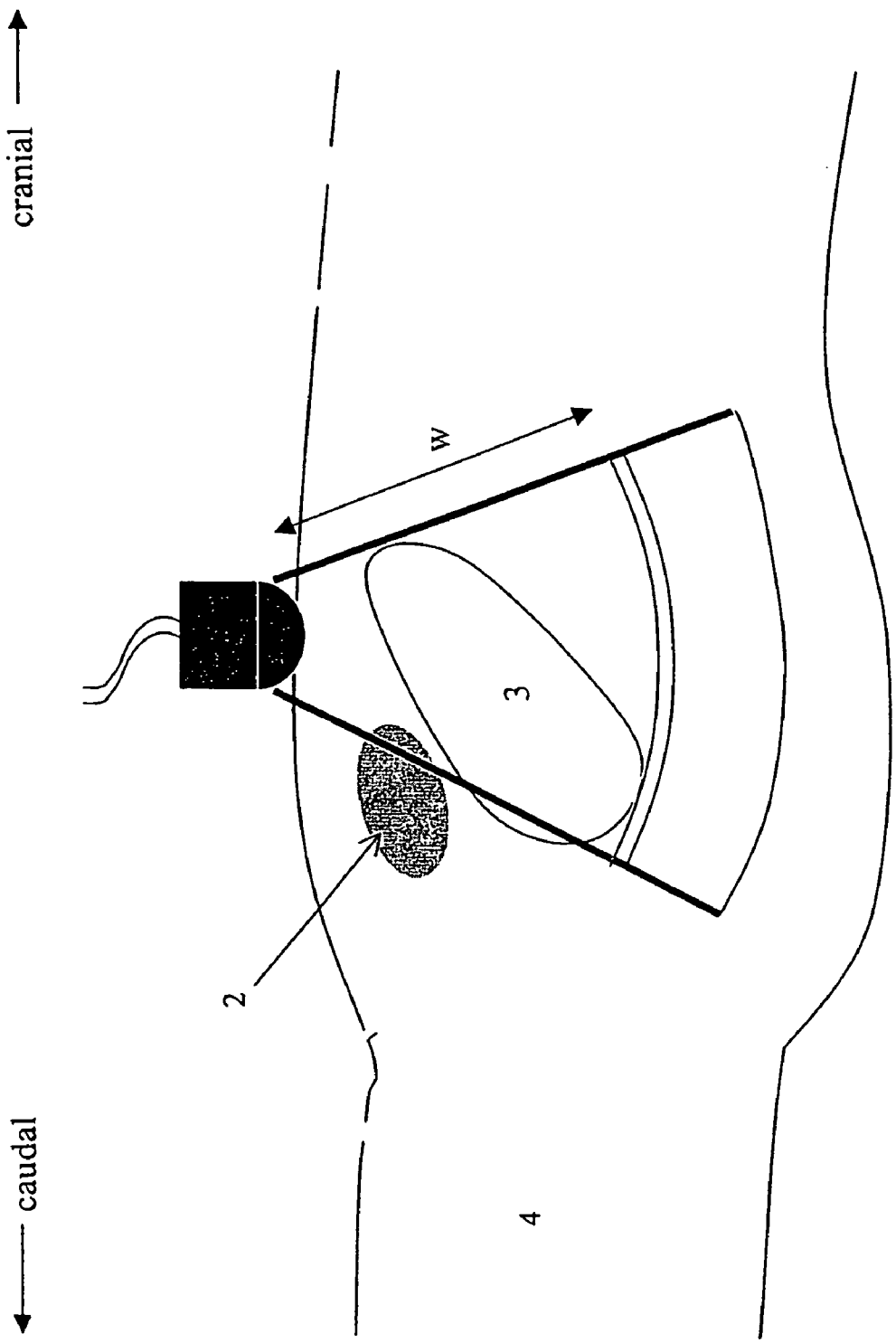
FIG. 7 Illustrates the sagittal cross sectional plane with a single wide beam transducer non-invasively positioned on the abdominal skin surface over the filled bladder 3. Echo signal is received from a range at depth W.

The schematic principle of transducer positioning is illustrated in FIG. 7. The sagittal cross section through the bladder is shown. The cone like shape of the acoustic beam allows to encompass approximately the full bladder volume, and therefore any harmonic distortion detected in the echo signal returning from a region beyond the posterior wall of the bladder around depth W, would correlate to the amount of fluid contained in the bladder.

It has been demonstrated that the propagation of ultrasound waves is a nonlinear process. The nonlinear effects, which increase with higher intensities, have been predicted and demonstrated at frequencies and intensities used in the diagnostic range either in water or in human body (A Baker et al: "Distortion and high-frequency generation due to non-linear propagation of short ultrasonic pulses from a plane circular piston", J Acoustic Soc Am 92(3), pp1699-1705). The distortion is due to slight non-linearities in sound propagation that gradually deform the shape of the propagating sound wave, and result in development of harmonic frequencies which were not present in the transmitted wave close to the transducer. This manifests itself in the frequency domain as the appearance of additional harmonic signals at integer multiples of the original frequency.

These effects occur most strongly when ultrasound waves propagate within liquids with relatively low acoustic attenuation such as water, amniotic fluid or urine. Indeed, acoustic propagation in fluids gives rise to extreme nonlinear effects at diagnostic frequencies. Within soft tissues, nonlinear processes also take place but are modified as a result of the different acoustic characteristics of these tissues, most notably their high acoustic absorption. Indeed, water and amniotic fluids (urine) are significantly different from tissue.

It is known from literature (A C Baker: "Prediction of non-linear propagation in water due to diagnostic medical ultrasound equipment", Phys Med Biol 1991 Vol 36, No 11, pp1457-1464; T Szabo et al: "Effects of non-linearity on the estimation of in-situ values of acoustic output parameters", J Ultrasound Med 18:33-41, 1999; M Hamilton et al: "Nonlinear acoustics", Academic Press) that the non-linearity of a medium is characterized by the coefficient of non-linearity $\beta$. Typical values for $\beta$ are 3.6 for water, 4 for blood and 6.5 for fatty tissue.

In addition to being nonlinear, all the media have acoustical loss due to absorption. The acoustical loss is described by the power law: $\alpha=\alpha_0 f^b$ where $\alpha_0$ is constant and b ranges from 1 to 2 depending on the medium. For water, the rate of absorption of an ultrasound wave propagating through it is quadratically related to the frequency (b=2). However, the rate of energy loss due to absorption is considered small and most of the time the dissipation-less theory is applicable over short ranges. However, biological media have large rates of energy loss and the frequency dependence has an exponential value of 1 to 1.5.

By considering both attenuation due to absorption loss and non-linearity, the exchange of energy between the two processes is complicated, because attenuation diminishes the amplitude of the generated harmonic components with propagation distance while non-linearity builds up these harmonics. So, harmonic distortion generally tends to enrich the higher harmonic components at the expense of the lower ones (energy transfer), while absorption damps out the higher components more rapidly than the lower ones. It is therefore difficult to reach a balance in which a given component loses as much energy by absorption as it gains from nonlinear distortion. Moreover, since the conditions for stability depend on the amplitude of the wave, which slowly decreases with propagation distance, the wave can never be completely stable, only relatively so.

The balance between the nonlinear process and the attenuation process is given by the Gol'dberg number Γ (Szabo et al), which represents a measure of which process dominates. When Γ=1, nonlinear effects are comparable to attenuation effects. If Γ is higher than 1, nonlinear processes dominate and when the Gol'dberg number is below 1, attenuation effects take over. As indication, for acoustic pressures of 500 kPa and 1MPa, at a transmit frequency of 3 MHz, the Gol'dberg number is respectively 86.5 and 43.2 for water. It is only 2.8 and 1.4 for liver-like tissue respectively at these pressures. For both settings, the parameter shows that for water, non-linearity is up to thirty times greater than for tissue.

The approach used here is based on the "non-linearity/attenuation" characteristic in differentiating between fluid media and soft tissue media. As described above, a single element transducer is placed in front of the bladder. The transducer generates a wide acoustic beam that is able to enclose the full bladder volume. Depending on the volume of urine contained in the bladder (bladder filling) and thus crossed by the acoustic beam, the amount of harmonic distortion generated in the back of the bladder will change. A radio frequency (RF) backscattered signal might be selected from a region of interest located preferably in the backside of the bladder. The amount of energy comprised in the second harmonic or higher harmonic components of the received RF echo signal can be extracted and correlated to the amount of volume of urine that has been encompassed by the acoustic beam. Since harmonic generation is different in tissue than in fluids, only the volume of urine that has been crossed by the acoustic beam would generate more harmonic energy. When the bladder is empty or below a certain volume level, no harmonic distortion occurs, whereas maximal distortion will be obtained for a full volume.

Figure 9:
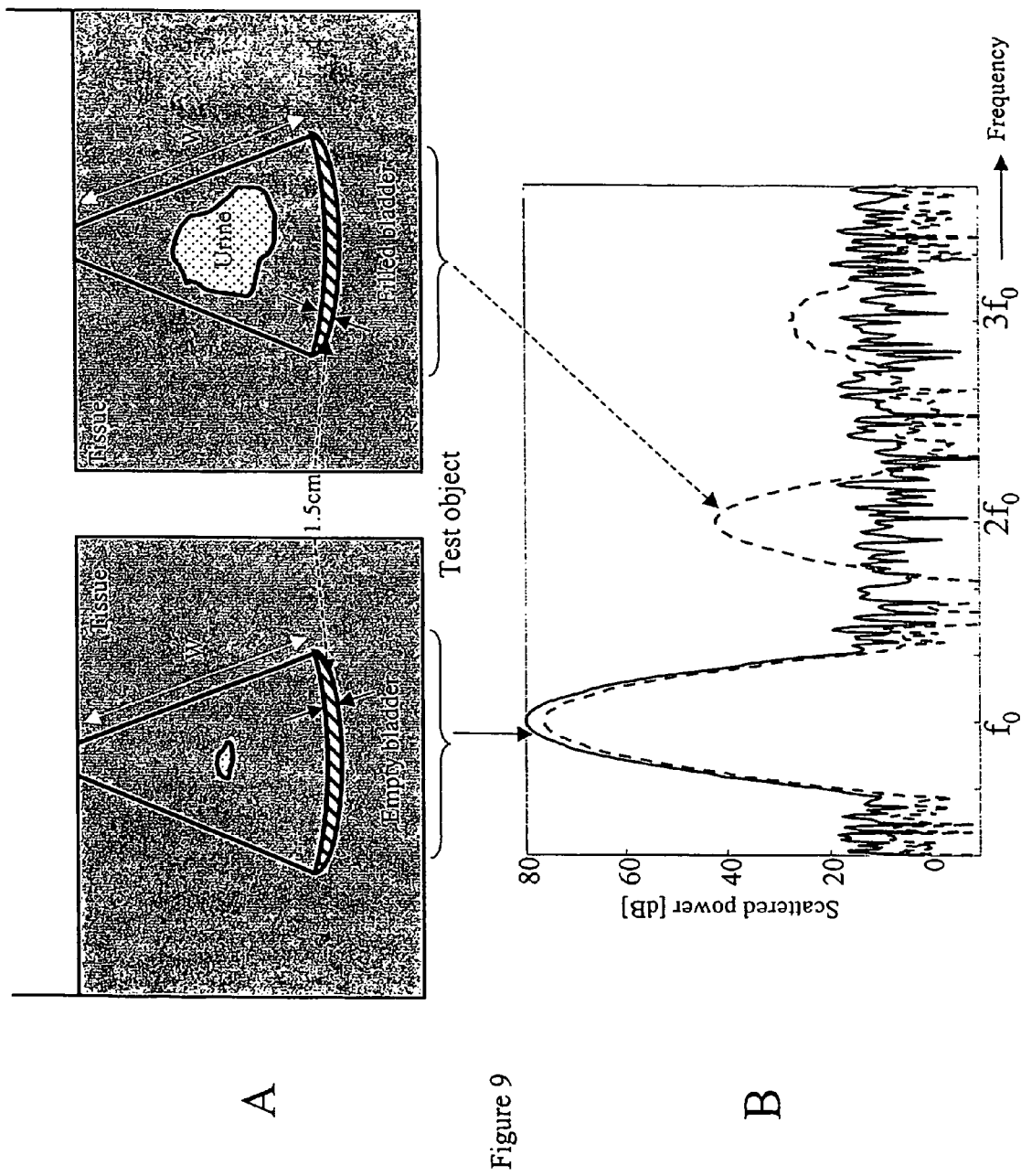
FIG. 9. Illustrates the measured received scattered power in the fundamental frequency $f_0$ and the higher harmonic frequencies $2f_0$ and $3f_0$ in a situation with an empty versus a filled bladder.

FIG. 9 illustrates the principle of the invention. Top panel shows two situations. The bladder is either empty (Panel A left side) or filled up with urine (Panel A right side). At a certain distance beyond the bladder (around 12 cm from the transducer), a region of interest of 1.5 cm width at depth W (see FIG. 7) is selected. Power spectra corresponding to echo signal recorded from the regions of interest are displayed in panel B.

The spectrum corresponding to the empty bladder (solid line) shows only a fundamental component. The harmonic distortion is very weak so that no harmonic frequencies are generated. However, the echo signal corresponding to the filled bladder situation (dashed line) demonstrates clear distortion where a second harmonic component with a significant energy is generated. The third harmonic component can be also present with lesser energy depending on the urine volume that has been crossed by the acoustic beam.

FIG. 9 demonstrates that depending on the volume contained in the bladder that the acoustic beam has intersected, the amount of generated second harmonic energy varies. When the acoustic beam crosses only tissue or when the volume of urine is very small, harmonic distortion is the lowest with no or very low harmonic energy. If the bladder is filled up or if the volume of urine is above a certain level (threshold), harmonics are generated. The generation of a harmonic component (second and/or higher harmonics) can be used for volume measurement, or simply as an indicator of filling of the bladder to a certain volume extent. The criterion can be such that if a certain amount of second harmonic (or higher harmonics) is generated in the echo signal, the device would indicate that the critical volume (or threshold) (say in adult patients around 450 ml) has been reached.

To avoid and eliminate any differences due to patient to patient variations, a normalization procedure needs to be performed a priori. Such a normalization procedure might consist of recording a first signal at very low transmit acoustic power from the same region of interest as described in the previous section. Such power would allow only linear propagation of the ultrasonic waves and avoid any harmonic generation. The echo signal would therefore have undergone only attenuation effects.

In the following transmit-receive sequence, the transmit acoustic power is increased with a certain factor (e) and a new recording is performed from the same region of interest. This measure with a much higher acoustic pressure is carried out to allow harmonic distortion to occur in the tissue. The echo signal in this case will undergo both attenuation and distortion effects. The first echo signal (linear case) will be re-scaled by the factor that corresponded to the increase in transmit power (e), and then used as a reference signal. Consequently, each patient has his own reference hence eliminating any variations such as obesity, inhomogeneities, etc.

Figure 8:
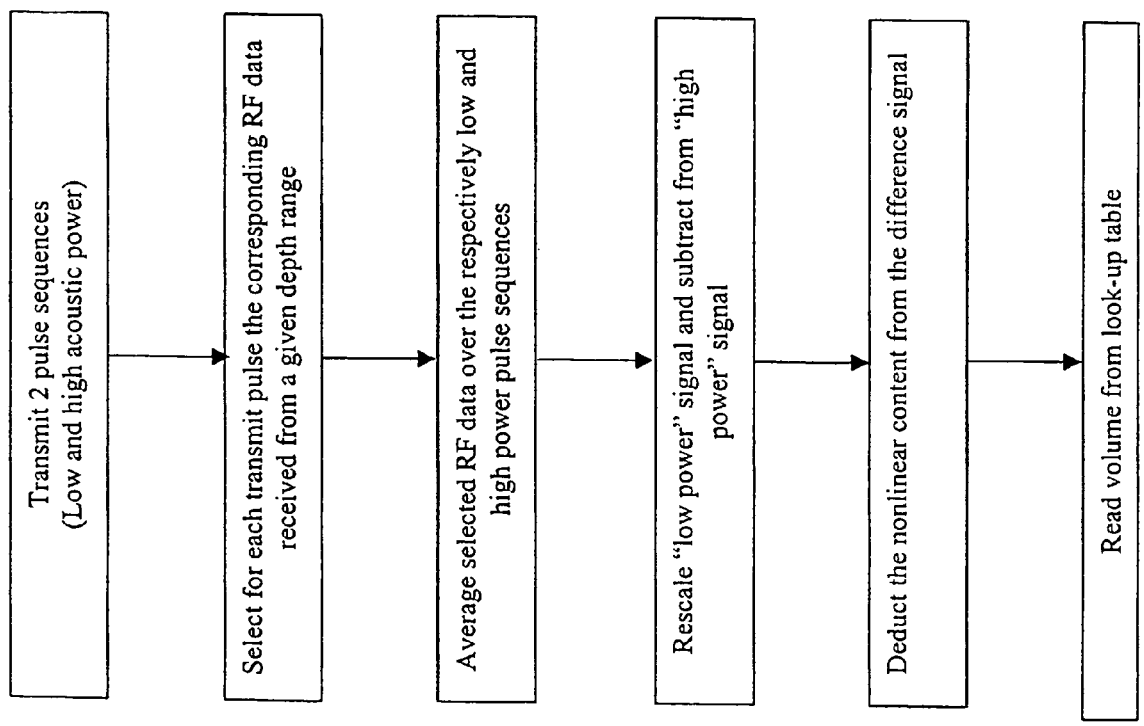
FIG. 8. Is a flow chart illustrating the principal steps taken by the bladder volume measurement instrument based on a single ultrasound wide beam where detection of presence of higher harmonics in the received signal from a give depth range is used to measure volume. Two different transmit levels are used to enhance the bladder effect and eliminate patient variation.
Figure 10:
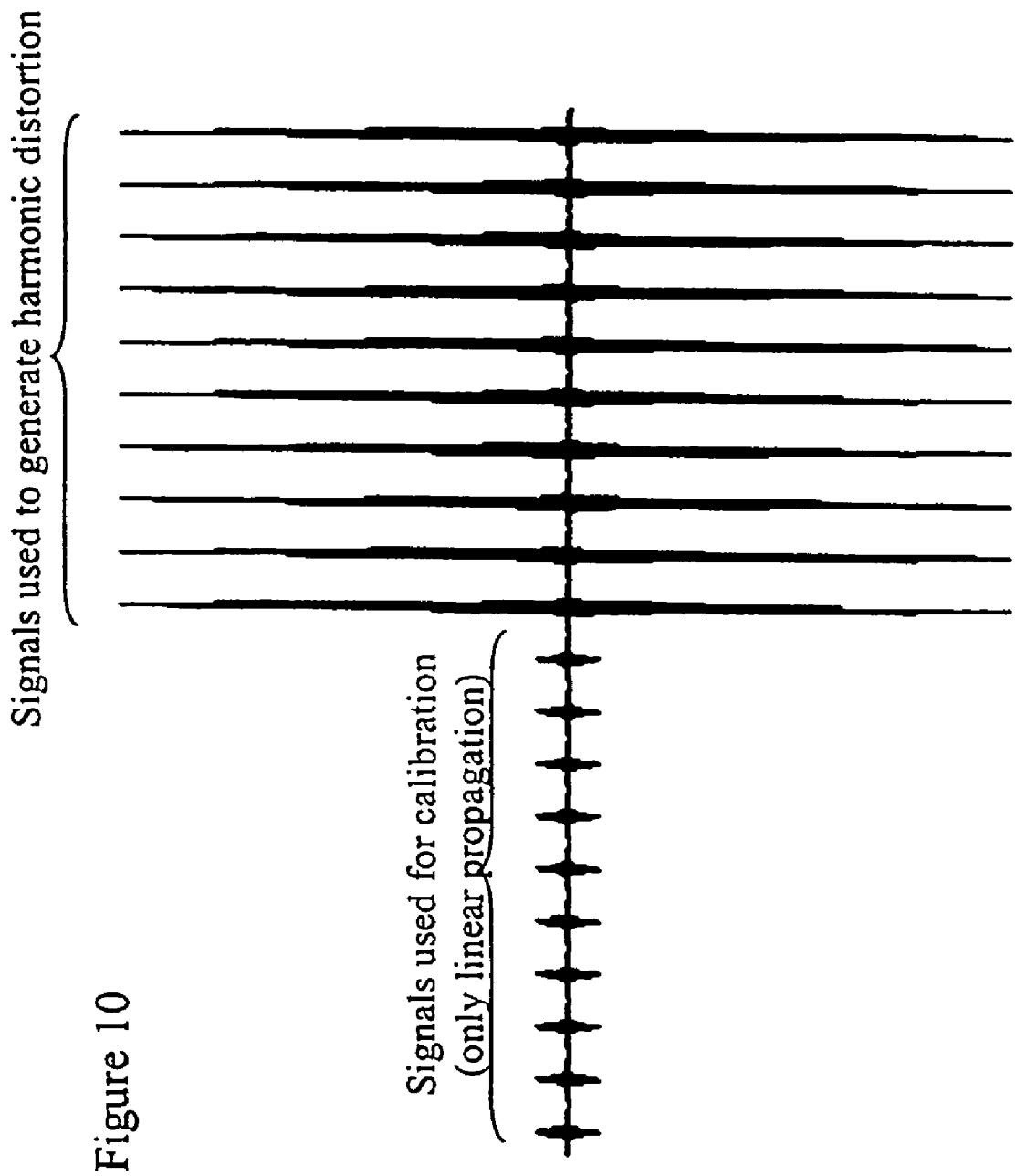
FIG. 10 shows two possible transmit pulse sequences to enhance the difference between linear and non-linear sound propagation.

A block diagram of a possible steps describing the second method is given in the flow chart of FIG. 8. The two transmitted signals might be transmitted with a very low repetition rate as indicated in FIG. 10. The first packet of transmit signals with low acoustic amplitude are used for calibration. The echoes received from those signals are averaged to reduce the noise level. The number of signals can be chosen such that a high signal-to-noise ratio is obtained. The second packet of signals with higher amplitudes are used to induce nonlinear propagation and harmonic distortion. The echoes received from these signals are averaged and then the harmonic energy is filtered and then compared to the calibration echo.

Figure 11:
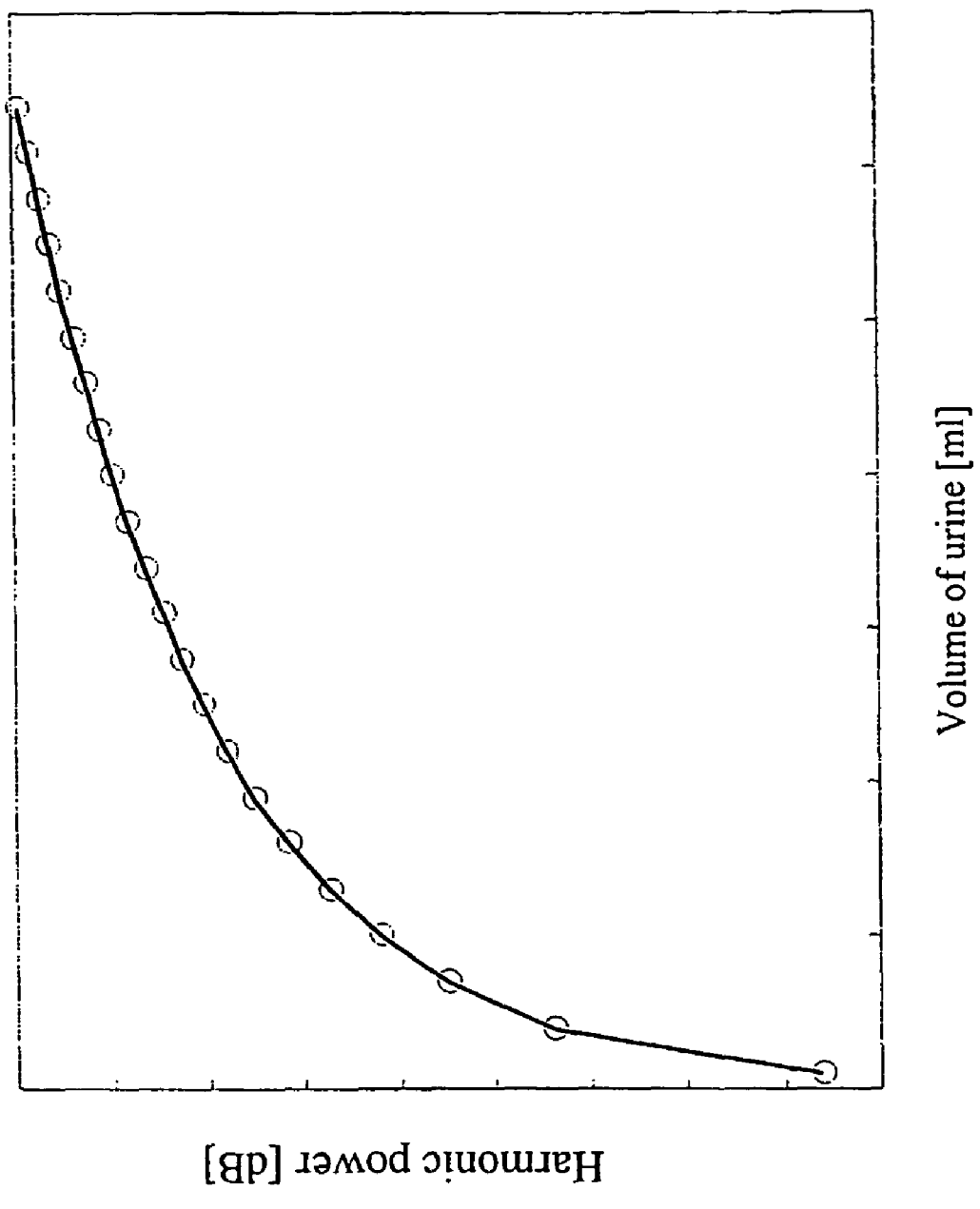
FIG. 11 Illustrates a possible look-up table based on prior calibrated patient bladder volume measurements relating presence of harmonic power in the received echo signal versus volume.

In order to estimate the volume of urine in the bladder, a look-up table can be created beforehand. Such a table, saved in the hard disk of the electronic device, will contain the correspondence between the harmonic energy and the volume of urine. Such a table can be extracted from a curve similar to the one given in FIG. 11. Such a curve can be obtained from a "learning" patient set of measurements. Look-up tables may eventually be produced for specific patient groups for age; gender and/or weight as an input parameter.

The described second method differs greatly from known other apparatus:

12) The device is composed of a single element defocused ultrasound transducer with a conical beam shape;
13) The single acoustic beam entirely encompasses the volumetric area of a possibly filled bladder.
14) The method is based on measurement of non-linear properties and attenuation behavior of propagating ultrasound waves as influenced by a urine filled bladder.
15) The method incorporates a technique to eliminate patient variation due to fat or skin properties.
16) The method for automatic volume computation does not assume any geometrical model for the bladder shape;
17) It is valid for any bladder shape since the received signal "integrates" all volume effects in the ultrasound beam.
18) All known other methods use bladder wall echoes as a basis to calculate volume.
19) The device works instantaneously.

Other embodiments are intentionally within the scope of the accompanying claims.

The invention claimed is:

1. An apparatus configured to measure a fluid volume contained in a body cavity comprising:
   at least one transducer assembly positioned in view of the body cavity and configured to transmit ultrasound to the body cavity, receive at least one echo reflected from surfaces associated with the body cavity; and
   a computer in signal communication with the at least one transducer assembly, the computer having access to a look-up table of data, the computer being configured to determine at least one harmonic energy level value associated with the at least one echo, the data describing a correspondence between the harmonic energy level value and the fluid volume, and to calculate the fluid volume contained in the body cavity based upon the data.

2. The apparatus of claim 1, wherein the body cavity comprises a bladder and the fluid comprises urine.

3. The apparatus of claim 1, wherein the at least one transducer assembly includes a plurality of transducer assemblies positioned for transmitting and receiving echoes in a selected order.

4. The apparatus of claim 3, wherein the plurality of transducer assemblies includes an array of five.

5. The apparatus of claim 4, wherein the array of five transducer assemblies are respectively oriented at angles OA, OB, OC, OD, OE, to an axis orthogonal to the plane of the transducer assemblies array, the angles being approximately OA=−25°, OB=0°, OC+25°, OO=+25°, OE=+40°.

6. The apparatus of claim 5, wherein the computer is configured to ascertain the fluid volume in terms of at least one of ranges of bladder filling and to indicate a clinically important bladder filling level.

7. The apparatus of claim 6, wherein the computer is coupled to a display to present within a look-up table of calibration factors inputted patient information, including at least one of gender, weight, age, and correction factors K derived from the look-up table of calibration factors.

8. The apparatus of claim 7, wherein the look-up table of calibration factors includes a calibration curve of ascertaining volume measurements from the acoustic power contained in the transmitted ultrasound to optimize correction factors K in a "self learning process".

9. The apparatus of claim 7, wherein volume information of the body cavity or the fluid may be frozen via a hold/start button connected with the at least one of the plurality of transducer assemblies.

10. The apparatus of claim 3, wherein the plurality of transducer assemblies are positioned so that the echo reflecting areas of the walls of the cavity are approximately located in a single cross-sectional sagittal plane.

11. The apparatus of claim 10, wherein the plurality of transducer assemblies are approximately disk-shaped.

12. The apparatus of claim 11, wherein the transducer assemblies are powered by a battery.

13. The apparatus of claim 10, wherein the transducer assemblies are configured to generate data enabling a display device to display correct caudal-cranial positioning of the transducer assemblies over a human bladder.

14. The apparatus of claim 1, wherein the at least one transducer assembly is connected with a cable to a housing containing an input device, a processor, a display and a power supply unit.

15. The apparatus of claim 1, wherein the at least one transducer assembly further includes an ultrasound coupling material covering the transducers for optimal acoustic coupling and patient convenience.

16. A method to determine a fluid volume occupying a body cavity comprising:
   positioning at least one transducer assembly in view of the body cavity;
   transmitting, with the at least one transducer assembly, ultrasound to the body cavity;
   receiving, with the at least one transducer assembly, at least one echo reflected from surfaces associated with the body cavity;
   accessing a look-up table of data;
   determining at least one harmonic energy level value associated with the at least one echo, the data describing a correspondence between the harmonic energy level value and the fluid volume; and
   calculating the fluid volume contained in the body cavity based upon the data.

17. The method of claim 16, wherein determining at least one harmonic energy level value associated with the echoes includes applying computer executable signal processing software with programmed instructions to differentiate information from fundamental and harmonic signals.

18. The method of claim 16, wherein positioning includes positioning an array of transducer assemblies configured to transmit ultrasonic beams into the subject with a predetermined spatial location and mounting angle.

19. The method of claim 18, wherein the array of transducer assemblies are acoustically coupled to the skin of the subject being measured using an acoustic coupling material.

20. An apparatus to determine a fluid volume occupying a bladder comprising:
   at least one transducer assembly positioned in view of the bladder and configured to transmit ultrasound of at least one acoustic power having a fundamental frequency to the bladder, receive echoes having a harmonic frequency and the fundamental frequency reflected from surfaces associated with the bladder, convert the fundamental and harmonic frequency echoes into fundamental and harmonic signals, and identifying from the fundamental and harmonic signals those deriving from echoes having reflected from the posterior wall of the bladder and transiting through the fluid volume and anterior wall of the bladder; and
   a computer in signal communication with the at least one transducer assembly, the computer having access to a look-up table of calibration factors and executable signal processing software with programmed instructions to determine at least one harmonic energy level value associated with the echoes and to measure a bladder height and a bladder depth and to calculate the fluid volume contained in the bladder based upon the at least one harmonic energy level value associated with an echo having passed through the fluid as a function of associating the bladder height and the bladder depth with the calibration factors in the look-up table.

21. The apparatus of claim 20, wherein the fluid volume comprises a urine volume.

22. The apparatus of claim 21, wherein the at least one transducer assembly is adapted to transmit a beam of ultrasound sufficient to entirely subtend the bladder.

23. The apparatus of claim 20, wherein the programmed instructions comprise signals derived from predetermined depth ranges for the determination of fluid volume in the bladder.

24. The apparatus of claim 22, wherein transducer assembly comprises a curved single active piezo-electric element, shaped to form ultrasound beams at least one of a sphere sector and a cone sector.

25. The apparatus of claim 24, wherein the ultrasound transducer assembly includes a wide-angle lens to distribute the ultrasound beams to approximately encompass the bladder.

26. The apparatus of claim 25, wherein the transducer assembly is adapted to transmit at a fundamental ultrasound frequency and is adapted to receive the fundamental and higher harmonic signals of the transmitted frequency.

27. The apparatus of claim 26, wherein the programmed instructions to determine at least one harmonic energy level value associated with the echoes include algorithms for determining the scattered power of higher harmonics in the received signal and comparing the scattered power with the backscattered power in the fundamental frequency to calculate the fluid volume.

28. The apparatus of claim 27, wherein the at least one acoustic power includes a low transmit power and a high transmit power to enhance bladder filling measurement and eliminate patient variation due to instance obesity using combined pulse sequences arising from the low transmit and high transmit powers.

29. The apparatus of claim 28, wherein the combined pulse sequences arise from echo signals at a depth close to the position of the average anterior bladder wall in determining the fluid volume to limit the effects of variation in the body proximal to the transducer assembly.

30. The apparatus of claim 29, wherein the combined pulse sequences arise from echo signals may be altered by varying the transmitted power in subsequent pulse transmissions, such that linear and non-linear echo signals from various depths can be compared to eliminate effects of patient variation.

31. The apparatus of claim 30, wherein the variation in calculating the fluid volume may be in the form of a calibration curve derived from the look up table.

32. The apparatus of claim 20, wherein the at least one transducer assembly include a display adapted to indicate a volume above a predetermined threshold level, the threshold level being determined according to a specified medical application.

33. The apparatus of claim 32, wherein the display indicates a filling below a predetermined threshold level, the threshold level being determined according to a specified medical application.

34. The apparatus of claim 20, wherein the at least one transducer assembly is housed separately and connected to the rest of the apparatus with a flexible cable.

35. The apparatus of claim 20, wherein the at least one transducer assembly comprises a combination of a first acoustic active surface for optimal transmission and reception at the fundamental frequency and second acoustic active surface for optimal reception of the harmonic echo signals.

36. The apparatus of claim 20, wherein the at least one transducer assembly comprises a plurality of ultrasound transducers mounted thereon for transmitting and receiving a plurality of ultrasound signals into the bladder at least one of plural angles of incidence and plural spatial locations for providing a narrow beam direction in the dorsal direction to detect the anterior and posterior bladder wall.

37. A method to determine a fluid volume occupying a body cavity comprising:
positioning at least one transducer assembly in view of a body cavity;
transmitting a fundamental ultrasound frequency of at least one acoustic power to the body cavity;
receiving echoes having the fundamental ultrasound frequency and at least one harmonic frequency thereof associated with the body cavity;
converting the received ultrasound echoes into fundamental signals and harmonic signals;
identifying among the fundamental and harmonic signals those being associated with select echoes having reflected from the posterior wall of the body cavity and transited through the fluid contained within the body cavity and the anterior wall of the body cavity;
determining at least one harmonic energy level value associated with the echoes;
measuring a height and a depth of the body cavity from signals derived from the select echoes; and
calculating a fluid volume contained in the cavity based upon the at least one harmonic energy level value associated the select echoes using calibration factors contained in a look-up table to convert the height and the depth to the fluid volume.

38. A method for detecting a body cavity of a subject, measuring the volume of the body cavity and a fluid volume contained in the body cavity comprising:
positioning at least one transducer assembly in view of the body cavity;
transmitting a fundamental ultrasound frequency of at least one acoustic power to the body cavity;
receiving echoes having the fundamental ultrasound frequency and at least one harmonic frequency thereof associated with the body cavity;
converting the received ultrasound echoes into fundamental signals and harmonic signals;
identifying among the fundamental and harmonic signals those being associated with select echoes having reflected from the posterior wall of the body cavity and transited through the fluid contained within the body cavity and the anterior wall of the body cavity;
measuring a height and a depth of the body cavity from signals derived from the select echoes;
determining boundary information of the cavity from the harmonic signals in terms of the depth, the height, and a correction factor, K obtainable from a look-up table; and
calculating the fluid volume from a calibration curve obtainable from the look-up table.

39. The method of claim 38, wherein the correction factor K is obtainable from the look up table and the calibration curve.

* * * * *